United States Patent
Banju

(10) Patent No.: US 9,144,430 B2
(45) Date of Patent: Sep. 29, 2015

(54) SURGICAL FORCEPS

(75) Inventor: Kazuo Banju, Hachioji-shi (JP)

(73) Assignee: OLYMPUS CORPORATION, Tokyo (JP)

( * ) Notice: Subject to any disclaimer, the term of this patent is extended or adjusted under 35 U.S.C. 154(b) by 353 days.

(21) Appl. No.: 13/208,009

(22) Filed: Aug. 11, 2011

(65) Prior Publication Data

US 2012/0078292 A1    Mar. 29, 2012

Related U.S. Application Data

(63) Continuation of application No. PCT/JP2010/071384, filed on Nov. 30, 2010.

(30) Foreign Application Priority Data

Mar. 11, 2010    (JP) .................. 2010-054950

(51) Int. Cl.
A61B 17/00    (2006.01)
A61B 17/29    (2006.01)
(Continued)

(52) U.S. Cl.
CPC .......... *A61B 17/29* (2013.01); *A61B 17/00234* (2013.01); *A61B 17/1227* (2013.01); *A61B 17/1285* (2013.01); *A61B 17/08* (2013.01); *A61B 17/10* (2013.01); *A61B 2017/00265* (2013.01); *A61B 2017/292* (2013.01); *A61B 2017/294* (2013.01); *A61B 2017/2911* (2013.01); *A61B 2017/2913* (2013.01);
(Continued)

(58) Field of Classification Search
CPC ..................... A61B 17/00234; A61B 17/1227; A61B 17/1285; A61B 17/29; A61B 17/08; A61B 17/10; A61B 10/06

USPC ................................................. 606/205–208
See application file for complete search history.

(56) References Cited

U.S. PATENT DOCUMENTS 2,034,785 A * 3/1936 Wappler ................... 606/127
4,721,116 A * 1/1988 Schintgen et al. ............. 600/564
(Continued)

FOREIGN PATENT DOCUMENTS

EP    1645237 A1    4/2006
EP    1836979 A1    9/2007
(Continued)

OTHER PUBLICATIONS

European Search Report dated Apr. 10, 2013 from corresponding European Patent Application No. 10 84 7498. 2.

*Primary Examiner* — Dianne Dornbusch
(74) *Attorney, Agent, or Firm* — Scully, Scott, Murphy & Presser, PC

(57) ABSTRACT

A surgical forceps includes: an insertion portion including, an internal space formed along a longitudinal axis, a distal end portion, and a proximal end portion; a grasping portion provided at the distal end portion of the insertion portion; an operation rod having one end and the other end and arranged in the internal space of the insertion portion, the one end being connected to the grasping portion; an operation portion provided at the proximal end portion of the insertion portion and connected to the other end of the operation rod, the operation portion being configured to operate a movement of the grasping portion; and a portion to be operated provided in the vicinity of the distal end portion of the insertion portion, and connected to the operation rod such that the operation rod is movable according to an operation by an external force.

13 Claims, 15 Drawing Sheets

(51) Int. Cl.
  *A61B 17/122* (2006.01)
  *A61B 17/128* (2006.01)
  A61B 17/08 (2006.01)
  A61B 17/10 (2006.01)

(52) U.S. Cl.
  CPC  *A61B 2017/2925* (2013.01); *A61B 2017/2927* (2013.01); *A61B 2017/2929* (2013.01); *A61B 2017/2931* (2013.01); *A61B 2017/2939* (2013.01); *A61B 2017/2946* (2013.01)

(56) References Cited

U.S. PATENT DOCUMENTS

| | | | | |
|---|---|---|---|---|
| 4,760,848 A | * | 8/1988 | Hasson | 606/206 |
| 4,976,723 A | * | 12/1990 | Schad | 606/170 |
| 5,478,351 A | * | 12/1995 | Meade et al. | 606/205 |
| 5,509,923 A | | 4/1996 | Middleman et al. | |
| 5,908,437 A | * | 6/1999 | Asano et al. | 606/205 |
| 5,968,074 A | * | 10/1999 | Prestel | 606/205 |
| 6,659,939 B2 | | 12/2003 | Moll et al. | |
| 7,628,792 B2 | * | 12/2009 | Guerra | 606/51 |
| 2007/0027469 A1 | | 2/2007 | Smith et al. | |
| 2007/0225754 A1 | * | 9/2007 | Measamer et al. | 606/205 |

FOREIGN PATENT DOCUMENTS

| | | |
|---|---|---|
| EP | 1849415 A2 | 10/2007 |
| JP | 4-507363 A | 12/1992 |
| JP | 7-508201 A | 9/1995 |
| JP | 10-192290 A | 7/1998 |
| JP | 2002-011019 A | 1/2002 |
| JP | 2009-213903 | 9/2009 |
| WO | WO 91/02493 | 3/1991 |
| WO | WO 94/00059 | 1/1994 |
| WO | WO 2007/016060 A2 | 2/2007 |

* cited by examiner

SURGICAL FORCEPS

CROSS REFERENCE TO RELATED APPLICATION

This application is a continuation application of PCT/JP2010/071384 filed on Nov. 30, 2010 and claims benefit of Japanese Application No. 2010-054950 filed in Japan on Mar. 11, 2010, the entire contents of which are incorporated herein by this reference.

BACKGROUND OF THE INVENTION

1. Field of the Invention

The present invention relates to a surgical forceps which is mainly operated by an assistant when a surgery is performed by operating treatment instruments inserted in a body through a plurality of trocars.

2. Description of the Related Art

In recent years, a laparoscopic surgery (hereinafter, also referred to as a surgery) for performing therapeutic treatment without opening the abdomen has been performed, for example, for the purpose of lowering invasion on a patient. In this surgery, a plurality of trocars 202, 203, and 204 are punctured into an abdominal cavity of a patient 201, as shown in FIG. 1.

Then, an endoscope 205 is inserted into the abdominal cavity through the trocar 202, an electrocautery scalpel 206 as an intra-body-cavity treatment instrument is inserted into the abdominal cavity through the trocar 203, and a grasping forceps 207 is inserted into the abdominal cavity through the trocar 204.

An operating surgeon 208 performs therapeutic treatment and the like while mainly observing an endoscopic image in the abdominal cavity which is displayed on a screen of a display apparatus 211, and an assistant 209 performs therapeutic treatment and the like while mainly observing an endoscopic image displayed on a display apparatus 212. Note that the reference numerals 213, 214 represent nurses. The reference numeral 215 represents a light source apparatus. The reference numeral 216 represents a control apparatus, and the control apparatus includes a function of a video processor for generating endoscopic images.

When dissection is performed, a plurality of trocars, for example, four trocars are punctured into the abdomen of a patient. One of the four trocars is used for an endoscope, and an endoscope for observation is inserted into the abdominal cavity through the trocar. Other three trocars are used for treatment instruments, and for example, a grasping forceps and an electrocautery scalpel which are operated by an operating surgeon are respectively inserted in two of the three trocars. In the remaining one trocar, a grasping forceps which is operated by an assistant is inserted, for example.

For example, Japanese Patent Application Laid-Open Publication No. 10-192290 discloses a surgical treatment instrument as a grasping forceps. In the surgical treatment instrument, when the operator operates a movable handle to slide an operation rod in an axis direction, and a pair of grasping members is revolved around a fulcrum pin, thereby causing a grasping portion to open and close.

In the above-described surgery, the operating surgeon and the assistant respectively take care of and operate the treatment instruments inserted through the three trocars.

For example, the operating surgeon operates the electrocautery scalpel while operating the grasping forceps to dissect a diseased part, and gives instructions to the assistant to grasp a tissue and to pull the grasped tissue, for example. On the other hand, the assistant appropriately operates the grasping forceps in accordance with the instruction by the operating surgeon, to support smooth proceeding of medical procedure. This causes the medical procedure to effectively proceed.

However, if the assistant is an inexperienced doctor, there is a case where the assistant cannot understand the instruction by the operating surgeon, and gets stuck during the surgery or operates the grasping forceps differently from the operating surgeon's desired operation.

U.S. Pat. No. 6,659,939 discloses a robotic surgery and a method of the same. A plurality of surgical robots are used in the robotic surgery. Each person in charge can operate each of the plurality of surgical robots, or one person can operate the plurality of robots. Therefore, the operating surgeon operates the plurality of robots, thereby being freed from the burden of giving instructions to the assistant or coaching the assistant. As a result, the operating surgeon is capable of focusing entirely on the surgery.

SUMMARY OF THE INVENTION

A surgical forceps according to one aspect of the present invention includes: an insertion portion including a longitudinal axis, an internal space formed along the longitudinal axis, a distal end portion configured to be inserted into and extracted from a body cavity, and a proximal end portion positioned outside the body cavity; a grasping portion provided at the distal end portion of the insertion portion and configured to grasp an object; an operation rod having one end and the other end and arranged in the internal space of the insertion portion so as to be movable in a direction of the longitudinal axis, the one end being connected to the grasping portion so as to be able to operate the grasping portion according to a movement of the operation rod in the direction of the longitudinal axis; an operation portion provided at the proximal end portion of the insertion portion and connected to the other end of the operation rod so as to be able to move the operation rod in the direction of the longitudinal axis, the operation portion being configured to operate a movement of the grasping portion; and a portion to be operated provided in the vicinity of the distal end portion of the insertion portion which is configured to be inserted into and extracted from the body cavity, the portion to be operated being connected to the operation rod such that the operation rod is movable in the direction of the longitudinal axis according to an operation by an external force.

DETAILED DESCRIPTION OF THE PREFERRED EMBODIMENT(S)

Hereinafter, embodiments of the present invention will be described with reference to drawings.

FIGS. 2 to 18 relate to one embodiment of the present invention. A configuration of an intra-abdominal cavity operation supporting forceps of the present embodiment will be described with reference to FIGS. 2 to 5, and an operation example of the intra-abdominal cavity operation supporting forceps will be described with reference to FIGS. 6 to 18.

Figure 1:
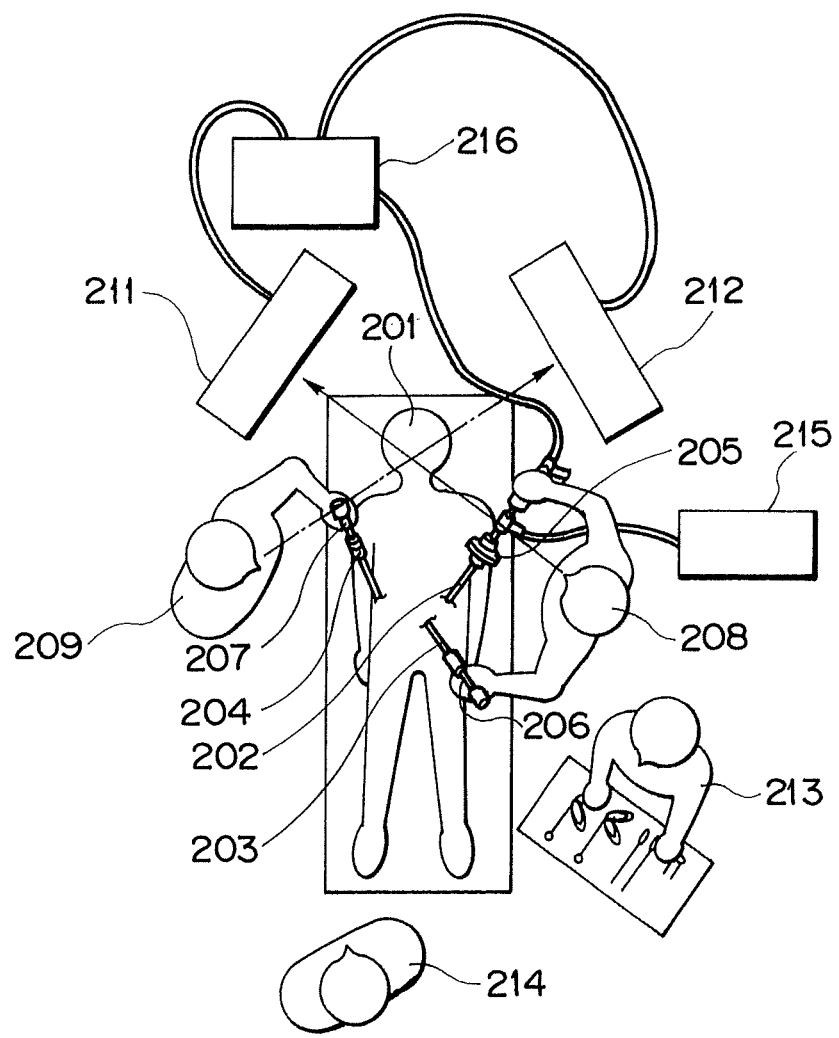
FIG. 1 is a view illustrating a laparoscopic surgery as one example of a surgery aimed at low invasion.
Figure 2:
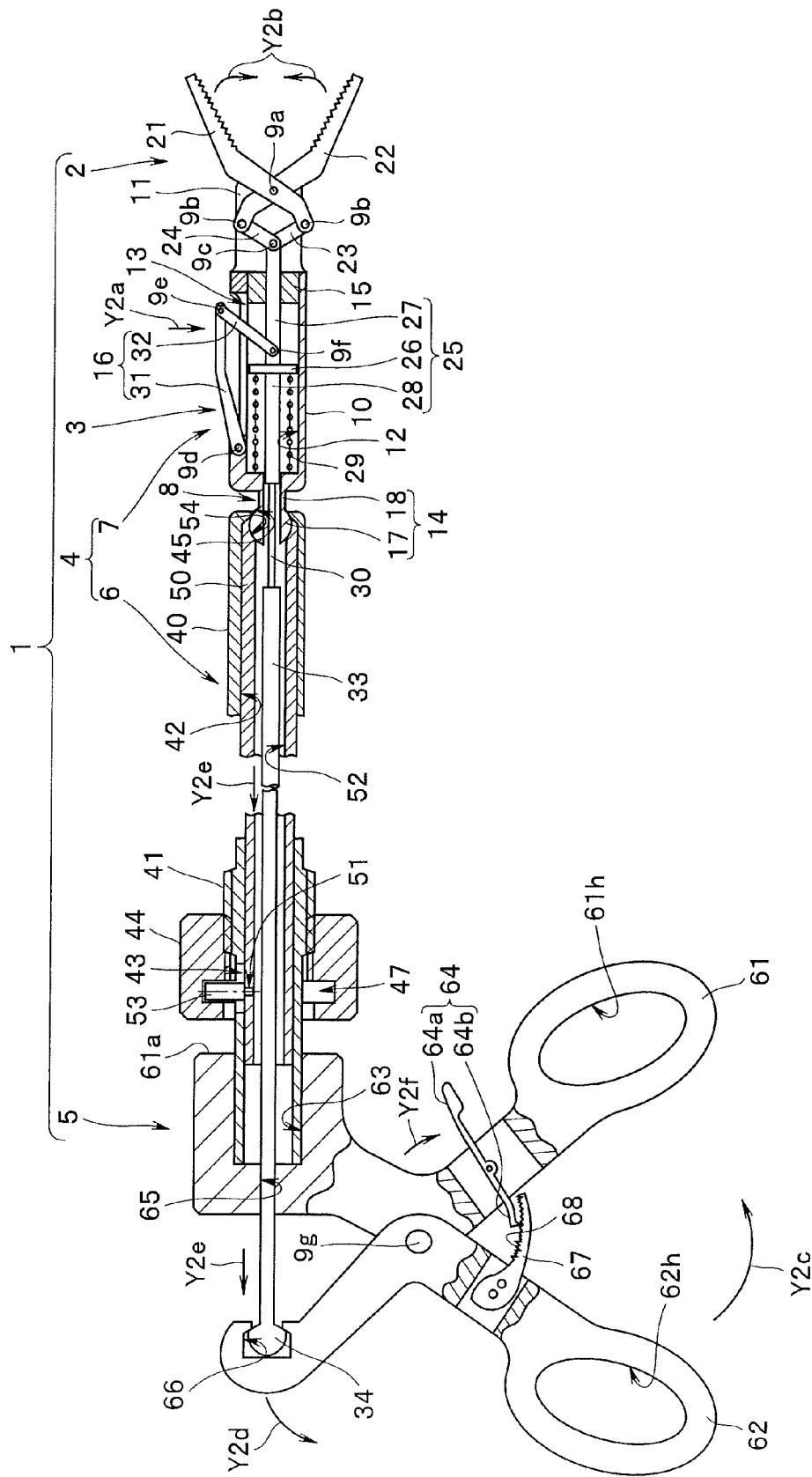
FIG. 2 relates to an exemplary configuration of an intra-abdominal cavity operation supporting forceps, and is an illustration diagram including a cross-sectional view illustrating a configuration of the intra-abdominal cavity operation supporting forceps.

An intra-abdominal cavity operation supporting forceps (hereinafter, described as surgical forceps) 1 according to the present embodiment as shown in FIG. 2 is a grasping forceps mainly operated by an inexperienced assistant when a surgery, in particular, a surgery under observation by an endoscope such as a laparoscopic surgery is performed.

The surgical forceps 1 is configured by including in the following order from the distal end side: a grasping portion 2; a grasping portion opening/closing operation portion 3; a treatment instrument insertion portion (hereinafter, shortly referred to as an insertion portion) 4; and a treatment instrument operation portion (hereinafter, shortly referred to as an operation portion) 5.

In the present embodiment, the insertion portion 4 includes an insertion portion main body 6 and a distal-end-side constituting portion 7. The insertion portion main body 6 and the distal-end-side constituting portion 7 are connected to each other so as to be flexible through a joint portion 8. Therefore, an operational force of a movable handle 62, to be described later, for opening and closing the grasping portion 2 is transmitted to a distal-end-side operation rod 25 to be described later through an operation rod main body 33 and a wire 30.

First, the configuration of the distal-end-side constituting portion 7 which constitutes the insertion portion 4 is described.

The distal-end-side constituting portion 7 is configured by including the grasping portion 2 and the grasping portion opening/closing operation portion 3 which are provided at a cylindrical opening/closing operation portion main body 10.

The opening/closing operation portion main body 10 includes a pair of distal-end-side projection pieces 11, an internal space (hereinafter, shortly referred to as a space) 12, a side hole 13, and a proximal-end-side protrusion 14. The pair of distal-end-side projection pieces 11 is projected in parallel from the distal end surface of the opening/closing operation portion main body 10. A first grasping member 21, a second grasping member 22 and the like, to be described later, which constitute the grasping portion 2 are disposed between the pair of projection pieces 11.

The space 12 is a round hole having a bottom surface, which is formed centering around a central axis of the opening/closing operation portion main body 10. A pushing spring 29 to be described later and the like are housed in the space 12. The opening of the space 12 is configured to be closed by a lid body 15. The lid body 15 includes a through hole. The through hole is formed centering around the central axis of the lid body 15.

The side hole 13 is formed on the side surface of the opening/closing operation portion main body 10, and communicates between the space 12 and outside. The side hole 13 is a so-called long hole formed parallel with the central axis of the opening/closing operation portion main body 10. The side hole 13 is provided with a grasping portion opening/closing mechanism 16, to be described later, configured by a link mechanism.

The proximal-end-side protrusion 14 protrudes from the proximal end surface of the opening/closing operation portion main body 10. The proximal-end-side protrusion 14 includes a spherical portion 17 and a shaft portion 18 which constitute the joint portion 8. The proximal-end-side protrusion 14 is provided with a through hole which communicates between the space 12 and outside. The through hole is formed centering around the central axis of the opening/closing operation portion main body 10.

Note that the opening/closing operation portion main body 10 according to the present embodiment is formed, or is configured to be formed by processing one rigid metal member or by resin molding.

When the opening/closing operation portion main body 10 is formed by one rigid metal member or by resin, the through hole is configured by a slit provided at the spherical portion 17 and a hole formed at the shaft portion 18. According to such a configuration, when the both side surfaces of the spherical portion 17 are pressed, the diameter dimension of the spherical portion 17 becomes smaller, and when the pressing of the both side surfaces is released, the diameter dimension of the spherical portion 17 returns to the original dimension.

In contrast, when the opening/closing operation portion main body 10 is configured by integrally fixing a plurality of rigid members by screwing, adhesive bonding, soldering, welding, or the like, the spherical portion 17 and the shaft portion 18 are separated bodies with respect to the opening/closing operation portion main body 10, for example, and the shaft portion 18 is integrally fixed to the proximal end portion of the opening/closing operation portion main body 10 by screwing, adhesive bonding, soldering, or welding.

The grasping portion 2 is configured by including, for example, a pair of grasping members 21, 22, a first fulcrum pin 9a, a pair of first rotation pins 9b, a pair of rotation members 23, 24, the distal-end-side operation rod (hereinafter, referred to as the first rod) 25, and a second rotation pin 9c.

The grasping members 21, 22 are formed in a predetermined flexed shape. The grasping members 21, 22 have grasping surfaces for grasping a tissue on the respective one end side surfaces. Each of the grasping members 21, 22 has a first through hole (not shown) through which the first fulcrum pin 9a is inserted and a second through hole (not shown) through which each of the first rotation pins 9b is inserted. The respective first through holes are formed at halfway positions separated from the respective end surfaces of the grasping members 21, 22 by a predetermined distance. On the other hand, the respective second through holes are formed at predetermined positions on the other end sides of the grasping members 21, 22.

Each of the rotation members 23, 24 has a first through hole (not shown) through which each of the first rotation pins 9b is inserted, and a second through hole (not shown) through which the second rotation pin 9c is inserted. The respective first through holes are formed at predetermined positions on one end sides of the rotation members 23, 24. The respective second through holes are formed at predetermined positions on the other end sides of the respective rotation members 23, 24. The first rod 25 includes at a halfway portion thereof a flange portion 26. The flange portion 26 is provided so as to be separated from the distal end surface by a predetermined distance. The first rod 25 is configured by including the flange portion 26, a distal end rod 27 which configures more distal end side than the flange portion 26, and a proximal end rod 28 which configures a more proximal end side than the flange portion 26.

The flange portion 26 is slidably arranged in the space 12 of the opening/closing operation portion main body 10. In this arranged state, the distal end rod 27 of the first rod 25 passes through the through hole of the lid body 15 to be projected outside. On the other hand, the proximal end rod 28 of the first rod 25 is arranged inside the through hole of the proximal-end-side protrusion 14. The first rod 25 is slidable with respect to the opening/closing operation portion main body 10.

The pushing spring 29 which is a coil spring is arranged as a biasing member in the space 12 so as to be located between the flange portion 26 and the bottom surface of the space 12. The pushing spring 29 has a biasing force to move the flange portion 26 in the direction of the lid body 15 which closes the opening of the space 12.

Note that a through hole (not shown) through which the second rotation pin 9c is inserted is formed at a predetermined position of the distal end rod 27.

In addition, at a predetermined position between the distal end surface of the distal end rod 27 and the flange portion 26, a through hole through which a fourth rotation pin to be described later (see reference numeral 9f of the drawing) is inserted is formed.

Furthermore, in the present embodiment, one end portion of the wire 30 having a preset flexibility is fixed onto the proximal end surface of the proximal end rod 28 by soldering, for example. The wire 30 passes through the through hole of the proximal-end-side protrusion 14 to be extended outward. The other end portion of the wire 30 is fixed to the distal end portion of an operation rod main body 33 to be described later by soldering, for example.

The grasping members 21, 22 are rotatably connected to each other by the first fulcrum pin 9a. The first rotation member 23 has one end side rotatably connected to the other end side of the grasping member 21 by one of the first rotation pins 9b. The second rotation member 24 has one end side rotatably connected to the other end side of the grasping member 22 by the other of the first rotation pins 9b. The grasping members 21, 22 constituting the grasping portion 2 are rotatably disposed at the opening/closing operation portion main body 10 by the first fulcrum pin 9a fixedly disposed on the pair of projection pieces 11 included in the opening/closing operation portion main body 10.

The other end side of the first rotation member 23 and the other end side of the second rotation member 24 are rotatably connected to the distal end rod 27 of the first rod 25 projected from the lid body 15, by the second rotation pin 9c. According to such a configuration, the grasping members 21, 22 which constitute the grasping portion 2 open and close in accordance with advancing and retracting of the first rod 25.

Specifically, the pair of grasping members 21, 22 of the grasping portion 2 is brought into an open state by moving the first rod 25 to the distal end side, and brought into a closed state by moving the first rod 25 to the proximal end side. In the present embodiment, the pushing spring 29 allows the flange portion 26 to move toward the lid body 15, thereby bringing the grasping members 21, 22 into an open state. On the other hand, the pushing spring 29 is compressed by the operation at hand of the movable handle 62 by the operator.

The grasping members 21, 22 are brought into a closed state by the pushing spring 29 being compressed. That is, the grasping members 21, 22 of the grasping portion 2 in the present embodiment are in the maximum open state in the initial state by the biasing force of the pushing spring 29.

The grasping portion opening/closing mechanism 16 has a transmitting member 31 and a rod moving bar 32. The transmitting member 31 is a first operating member and formed in a predetermined flexed shape, a bending shape, or the like, for example. The transmitting member 31 has a first through hole (not shown) through which a second fulcrum pin 9d is inserted, and a second through hole (not shown) through which a third rotation pin 9e is inserted.

The rod moving bar 32 is a second operating member and formed in a straight shape. The rod moving bar 32 has a first through hole (not shown) through which the third rotation pin 9e is inserted, and a second through hole (not shown) through which the fourth rotation pin 9f is inserted.

One end portion of the transmitting member 31 is rotatably arranged on the proximal end side in the side hole 13 by the second fulcrum pin 9d. One end side of the rod moving bar 32 is rotatably connected to the other end side of the transmitting member 31 by the third rotation pin 9e. The other end side of the rod moving bar 32 is rotatably connected to the distal end rod 27 by the fourth rotation pin 9f. In this connected state, the intersecting angle between the transmitting member 31 and the rod moving bar 32 is an acute angle.

The grasping portion opening/closing mechanism 16 causes the grasping members 21, 22 to respectively move in the directions shown by the arrows Y2b when an external force in the direction shown by the arrow Y2a in the drawing acts on the transmitting member 31. Specifically, when the external force in the direction shown by the arrow Y2a in the drawing acts on the transmitting member 31, the transmitting member 31 is rotated in a clockwise direction in the drawing around the second fulcrum pin 9d and moved toward inside of the side hole 13. Then, the rod moving bar 32 rotates around the third rotation pin 9e in accordance with the rotational movement of the transmitting member 31, which makes the intersecting angle smaller. At this time, the first rod 25 retracts against the biasing force of the pushing spring 29. Then, the grasping members 21, 22 respectively move in the directions shown by the arrows Y2b in accordance with the retracting of the first rod 25.

Figure 3:
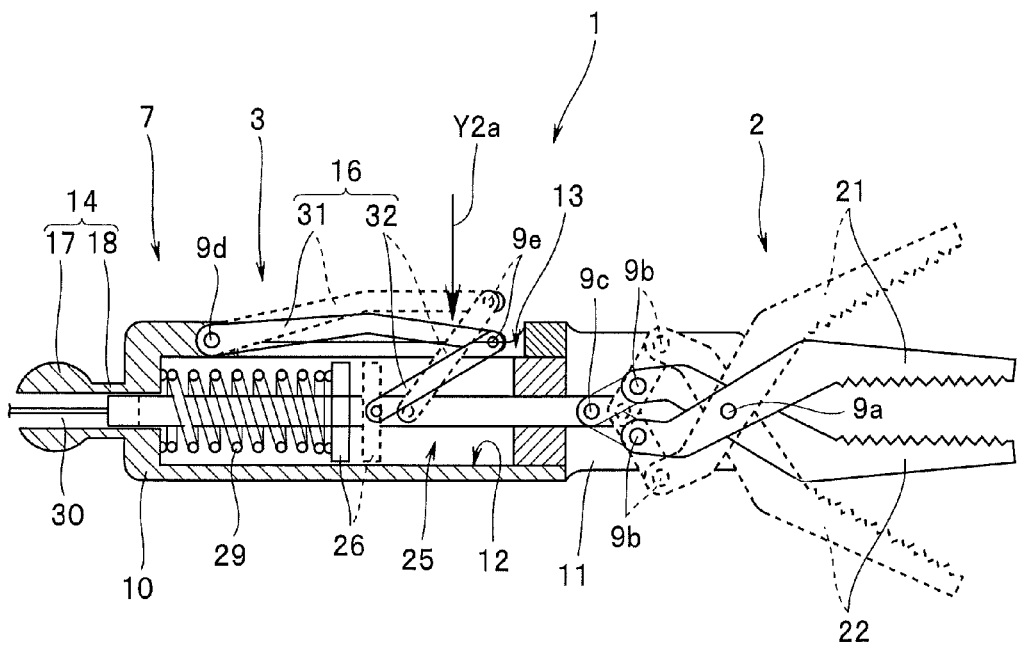
FIG. 3 is an enlarged view of a distal-end-side constituting portion of the intra-abdominal cavity operation supporting forceps, for mainly illustrating a working of the distal-end-side constituting portion.

That is, when the grasping members 21, 22 of the grasping portion 2 are in the maximum open state by the biasing force of the pushing spring 29 as shown by the dashed lines in FIG. 3, the external force in the arrow Y2a direction for moving the transmitting member 31 toward inside the side hole 13 is acted on the transmitting member 31 which constitutes the grasping portion opening/closing mechanism 16 of the grasping portion opening/closing operation portion 3. Then, the grasping members 21, 22 in the maximum open state are gradually closed and the grasping surface of the first grasping member 21 and the grasping surface of the second grasping member 22 get close to each other, thereby being changed into a state for allowing a tissue to be grasped.

Next, a configuration of the insertion portion main body 6 constituting the insertion portion 4 will be described.

The insertion portion main body 6 includes an elongated insertion portion external body 40 and a flexed state fixing rod (hereinafter, referred to as a fixing rod) 50.

As shown in FIG. 2, the insertion portion external body 40 is an elongated rigid cylindrical member. The proximal end portion of the insertion portion external body 40, at which an opening is formed, is integrally fixed by screwing, adhesive bonding, soldering, welding, or the like, to an insertion portion external body hole 63 of a fixed handle 61, to be described later, which constitutes the operation portion 5.

The insertion portion external body 40 includes a male screw portion 41, a fixing rod space 42, and a rod moving hole 43. The male screw portion 41 is provided at a position separated from a handle distal end surface 61a of the fixed handle 61 by a predetermined distance. A joint fixing knob 44, to be described later, having a female screw is screwed with the male screw portion 41.

The fixing rod space 42 is a hole having a bottom surface which is formed centering around the central axis of the insertion portion external body 40. In the fixing rod space 42, the fixing rod 50 and the spherical portion 17 are housed. The distal end portion of the insertion portion external body 40 has a through hole which communicates between the fixing rod space 42 and outside and configures the joint portion 8. The through hole is formed centering around the central axis of the insertion portion external body 40.

Figure 4:
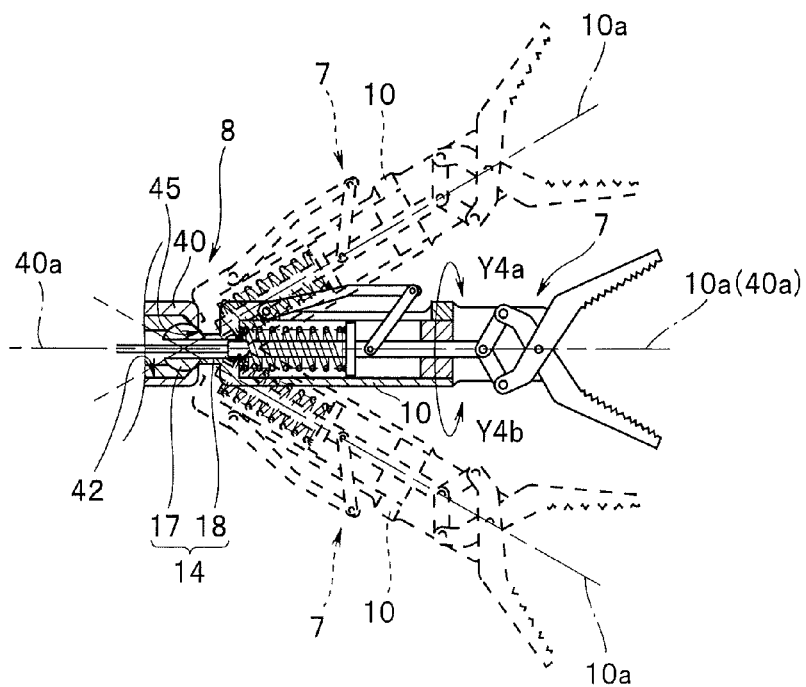
FIG. 4 is a view illustrating a working of a joint portion of the intra-abdominal cavity operation supporting forceps, for illustrating a linear state in which a central axis of an opening/closing operation portion main body and a central axis of an insertion portion external body coincide with each other, and a flexed state in which the central axes intersect with each other.

As shown in FIG. 2 and FIG. 4, one opening of a distal-end through hole 45 is formed on the bottom surface of the fixing rod space 42. The bottom surface is formed having a curved surface on which the spherical portion 17 is slidable, or an inclined surface with which the spherical portion 17 is brought into contact.

As shown in FIG. 4, in the state where the spherical portion 17 constituting the proximal-end-side protrusion 14 is arranged in the distal-end through hole 45 of the insertion portion external body 40, the opening/closing operation portion main body 10 can revolve around a central axis 40a of the insertion portion external body 40, that is, in the arrow Y4a direction and in the arrow Y4b direction against the wire 30, by an external force.

In addition, the opening/closing operation portion main body 10 changes between a linear state shown by the solid lines in FIG. 4 and a flexed state shown by the dashed lines in FIG. 4. In the linear state, a central axis 10a of the opening/closing operation portion main body 10 and the central axis 40a of the insertion portion external body 40 coincide with each other. The spherical portion 17 is slid with respect to the distal-end through hole 45 by an external force, which provides the flexed state in which the central axis 10a of the opening/closing operation portion main body 10 intersects with the central axis 40a of the insertion portion external body 40.

The central axis 10a is the central axis of the distal-end-side constituting portion 7 and the central axis 40a is the central axis of the insertion portion main body 6.

Figure 5:
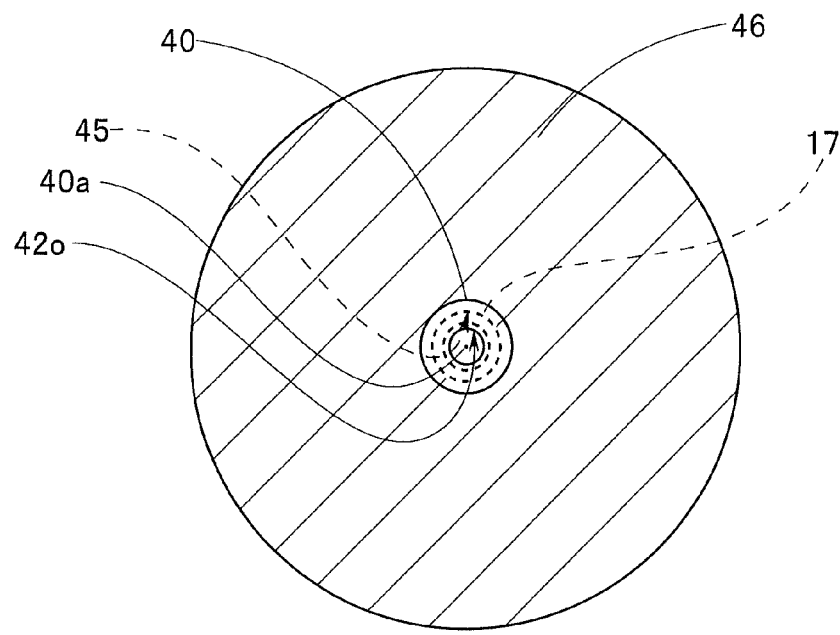
FIG. 5 is a view illustrating an arranging region of a grasping portion provided at a distal end of the insertion portion having the joint portion.

In the flexed state in which the central axis 10a of the opening/closing operation portion main body 10 and the central axis 40a of the insertion portion external body 40 intersect with each other, the grasping portion 2 can be arranged in a region 46 shown by the diagonal lines in FIG. 5, that is, a position in up, down, left, or right direction, a position between the up direction and the right direction, or a position between the down direction and the left direction, with the central axis 40a of the insertion portion external body 40 as a center.

Note that the region 46 is adjustable by appropriately setting a diameter dimension of the shaft portion 18 inserted through the distal-end through hole 45, and the length dimension of the shaft portion 18, that is, the separation distance between the distal end surface of the insertion portion external body 40 and the proximal end surface of the opening/closing operation portion main body 10. In addition, the reference numeral 42o in FIG. 5 represents the other opening of the through hole. Specifically, the other opening 42o is an opening of the distal-end through hole 45, which is formed on the distal end surface of the insertion portion external body 40.

As shown in FIG. 2, at least one rod moving hole 43 is formed on the side surface of the insertion portion external body 40 so as to be located on the more proximal end side than the male screw portion 41, for example. The rod moving hole 43 is a so-called long hole formed parallel with the central axis of the insertion portion external body 40. The rod moving hole 43 communicates between the fixing rod space 42 and outside. A fixing rod moving pin 53, to be described later, is projected from the rod moving hole 43.

In the present embodiment, the insertion portion external body 40 is a cylindrical member. However, the insertion portion external body may be formed by an elongated rigid pipe member and a cylindrical member having a predetermined length dimension which constitutes the distal end portion of the insertion portion external body 40. The cylindrical member is integrally fixed to one end surface side of the pipe member by screwing, adhesive bonding, soldering, welding, or the like. The bottom surface of the cylindrical member has a curved surface on which the spherical portion 17 is slidable, or an inclined surface with which the spherical portion 17 is brought into contact, and has one opening of the distal-end through hole 45 formed thereon.

The fixing rod 50 is a holding mechanism and arranged in the fixing rod space 42 of the insertion portion external body 40. The entire length of the fixing rod 50 is set to a predetermined dimension for allowing the fixing rod 50 to be slidable in the fixing rod space 42. The fixing rod 50 includes a female screw portion 51 and an operation rod main body space 52. The female screw portion 51 is provided on the outer circumferential surface of the fixing rod 50. The female screw portion 51 is screwed with the male screw portion of the fixing rod moving pin 53 through the rod moving hole 43 of the insertion portion external body 40.

The operation rod main body space 52 is a hole having a bottom surface formed centering around the central axis of the fixing rod 50, and has an opening arranged on the side of the operation portion 5. The wire 30 and the operation rod main body 33 are inserted through the operation rod main body space 52. Therefore, a through hole in the axis direction, which communicates between the operation rod main body space 52 and outside, is formed at the distal end portion of the fixing rod 50. The distal-end-surface-side opening of the fixing rod 50, which is one opening configuring the through hole, is formed as a pressing surface 54 which abuts the spherical portion 17. That is, the fixing rod 50 has on the distal end surface thereof the pressing surface 54 which abuts to press the spherical portion 17.

The fixing rod 50 advances or retracts in the fixing rod space 42. Specifically, the fixing rod 50 moves forward or rearward by advancing or retracting, along the rod moving hole 43, the fixing rod moving pin 53 which is screwed to the fixing rod 50 and projected from the outer circumferential surface of the insertion portion external body 40 through the rod moving hole 43.

The assistant then moves the fixing rod moving pin 53 toward the distal end side of the rod moving hole 43, for example, thereby allowing the pressing surface 54 of the fixing rod 50 to abut the spherical portion 17 arranged in the distal-end through hole 45 of the insertion portion external body 40 and to press the spherical portion 17.

Note that the pressing force from the pressing surface 54 which abuts the spherical portion 17 increases, thereby capable of maintaining the linear state in which the central axis 10a of the opening/closing operation portion main body 10 and the central axis 40a of the insertion portion external body 40 coincide with each other or the flexed state in which the central axes intersect with each other.

In the present embodiment, the fixing rod moving pin 53 is arranged in an inner circumferential groove 47 which is provided to the joint fixing knob 44 screwed to the male screw portion 41 of the insertion portion external body 40.

The joint fixing knob 44 has a dual structure including an advancing/retracting member and a pressing member, for example, though illustration thereof is omitted. The advancing/retracting member is a ring-shaped member having the female screw portion to be screwed with the male screw portion 41. On the other hand, the pressing member has a through hole into which the insertion portion external body 40 is loosely arranged, and has on one end surface side a recessed portion which configures the inner circumferential groove 47 into which the fixing rod moving pin 53 is arranged. The advancing/retracting member and the pressing member are integrated by adhesive bonding or with a fixing screw, for example, and configured as the joint fixing knob 44.

The joint fixing knob 44 is rotated in the clockwise direction viewed from the proximal end side of the operation portion, for example, thereby being moved to the distal end side of the insertion portion external body 40. In accordance with the movement of the joint fixing knob 44 toward the distal end side, the fixing rod moving pin 53 moves in the rod moving hole 43 toward the distal end side, and the fixing rod 50 moves in the fixing rod space 42 toward the distal end side. That is, in accordance with the rotation of the joint fixing knob 44, the pressing surface 54 gradually comes closer to the spherical portion 17 and abuts the spherical portion 17. After the abutment, the pressing force applied from the pressing surface 54 to the spherical portion 17 gradually increases in accordance with the rotation. As a result, the joint portion 8 is pressed and held in the linear state or in the flexed state.

On the other hand, the joint fixing knob 44 is rotated in the counterclockwise direction viewed from the proximal end side of the operation portion, for example, thereby being moved toward the side of the operation portion 5. That is, the fixing rod 50 moves in the fixing rod space 42 toward the proximal end side in accordance with the movement of the joint fixing knob 44 to the side of the operation portion 5. As a result, in accordance with the rotation of the joint fixing knob 44, the pressing surface 54 gradually gets away from the spherical portion 17, and thereby the pressing force of the pressing surface is gradually decreased.

Finally, the configuration of the operation portion 5 is described.

The operation portion 5 is configured by including the fixed handle 61 and the movable handle 62. The movable handle 62 is rotatably connected to the fixed handle 61 by a connection pin 9g.

The fixed handle 61 includes the insertion portion external body hole 63 and a ratchet release lever 64. The ratchet release lever 64 includes an operation portion 64a and a pawl portion 64b which configures a ratchet mechanism. The ratchet release lever 64 is rotatably attached at a predetermined position in the vicinity of a finger hooking hole 61h of the fixed handle 61, for example, with the pawl portion 64b oriented toward the movable handle 62.

The insertion portion external body hole 63 is a hole for integrally fixing the proximal end portion of the insertion portion external body 40 to the fixed handle 61. The insertion portion external body hole 63 is formed so as to have a predetermined depth dimension from a handle distal end surface 61a.

The insertion portion external body hole 63 communicates with outside through a rod through hole 65. The operation rod main body 33 which is inserted in the operation rod main body space 52 of the fixing rod 50 and extended from the insertion portion external body 40 is advanceably/retractably inserted through the rod through hole 65. The central axis of the rod through hole 65 and the central axis of the insertion portion external body hole 63 are coaxial.

The movable handle 62 includes an operation rod disposing hole 66 and a rack portion 67. The rack portion 67 has a teeth portion 68 which configures the ratchet mechanism. The rack portion 67 is fixed at a predetermined position in the vicinity of a finger hooking hole 62h of the movable handle 62, for example.

The operation rod disposing hole 66 is a hole for attaching a substantially spherical-shaped projection portion 34, which is provided at the proximal end of the operation rod main body 33, to the movable handle 62. The operation rod disposing hole 66 is configured by a recessed portion, for example, and an opening of the recessed portion is sealed by a ring member (not shown) having a through hole through which the operation rod main body 33 is loosely inserted. This prevents the projection portion 34 from falling off from the operation rod disposing hole 66.

In the present embodiment, when an assistant performs operation for moving the movable handle 62 in the arrow Y2c direction, for example, the side of the movable handle 62, which is closer to the operation rod disposing hole 66, is moved in the arrow Y2d direction. Since the projection portion 34 is disposed in the operation rod disposing hole 66, the operation rod main body 33 moves in the arrow Y2e direction. Then, in accordance with the movement of the operation rod main body 33, the wire 30 and the first rod 25 are pulled against the biasing force of the pushing spring 29, thereby bringing the grasping surfaces of the grasping members 21, 22 into contact with each other.

At this time, the rack portion 67 which configures the ratchet mechanism moves in accordance with the movement of the movable handle 62, which changes the positional relationship between the pawl portion 64b and the teeth portion 68. When the movement of the movable handle 62 in the arrow Y2c direction is stopped, the movable handle 62 is held at a moved position by the ratchet mechanism.

Note that, in a case where the movable handle 62 is moved in the direction opposite to the arrow Y2c direction, the assistant moves the operation portion 64a of the ratchet release lever 64 in the arrow Y2f direction, for example, thereby releasing the engaged state between the pawl portion 64b and the teeth portion 68.

A usage pattern of the surgical forceps 1 configured as described above is described.

Figure 6:
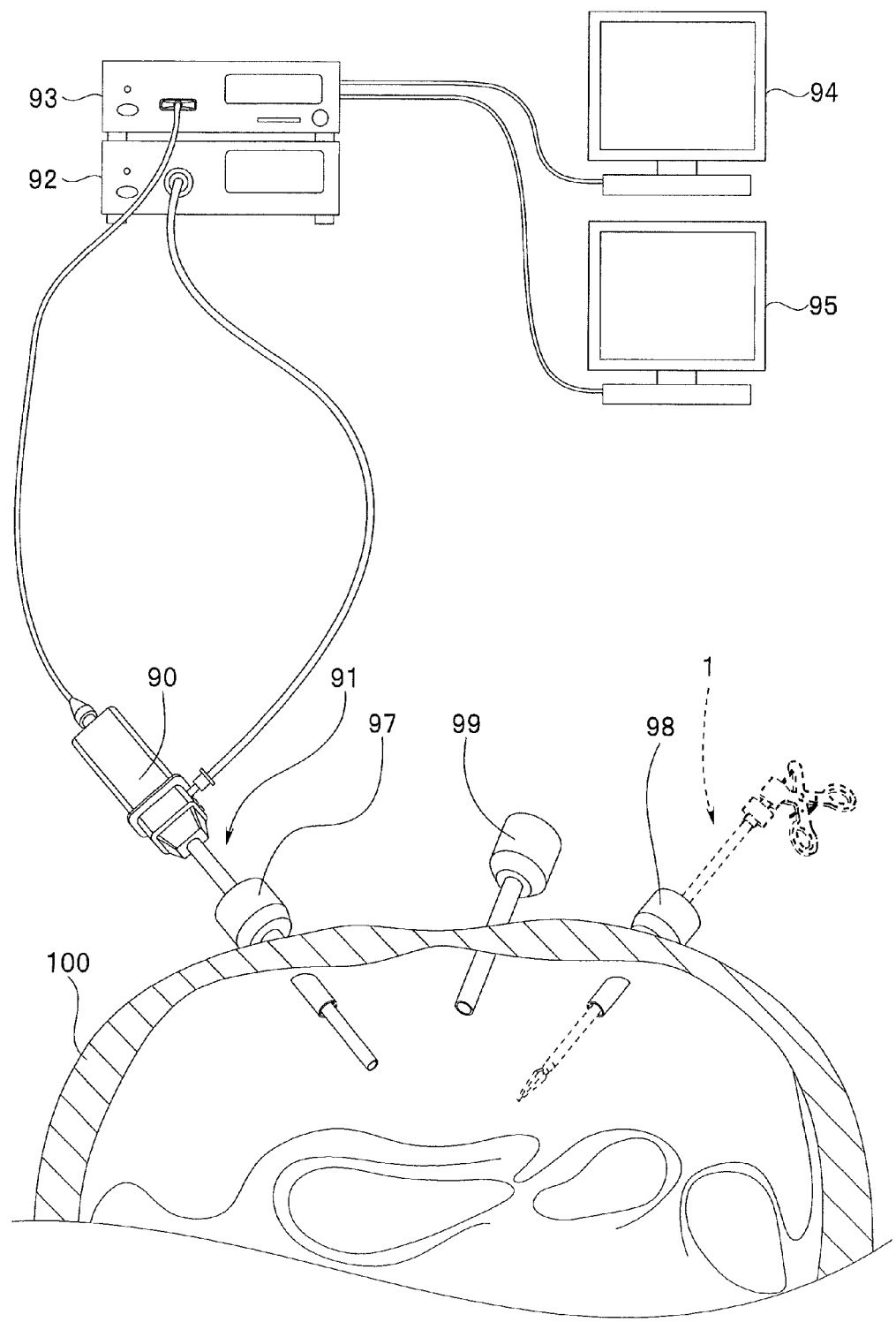
FIG. 6 is a view illustrating a laparoscopic surgical system.

When performing an intra-abdominal surgery, for example, a staff member prepares a rigid endoscope 91, a light source apparatus 62, a camera control unit 93, a first display apparatus 94, and a second display apparatus 95, as shown in FIG. 6. In addition, in constructing the laparoscopic surgical system, the staff member prepares, as treatment instruments, for example, an electrocautery scalpel (not shown), a grasping forceps (the reference numeral 96 in FIG. 7) which are handled by the operating surgeon and the surgical forceps 1 used by the assistant, and also prepares a plurality of trocars 97, 98, 99, etc., and the like.

In the present embodiment, the rigid endoscope 91 has at the proximal end portion thereof an eye piece to which a rigid endoscope camera 90 is attached. An optical image of a region to be observed which is illuminated by the illumination light supplied from the light source apparatus 92 to the rigid endoscope 91 is picked up by the rigid endoscope camera 90 attached to the eye piece.

The first display apparatus 94 is a liquid crystal display for displaying an endoscopic image picked up by the rigid endoscope camera 90, for example, and is observed by the operating surgeon. The second display apparatus 95 is a liquid crystal display for the assistant to observe the same endoscopic image.

Figure 7:
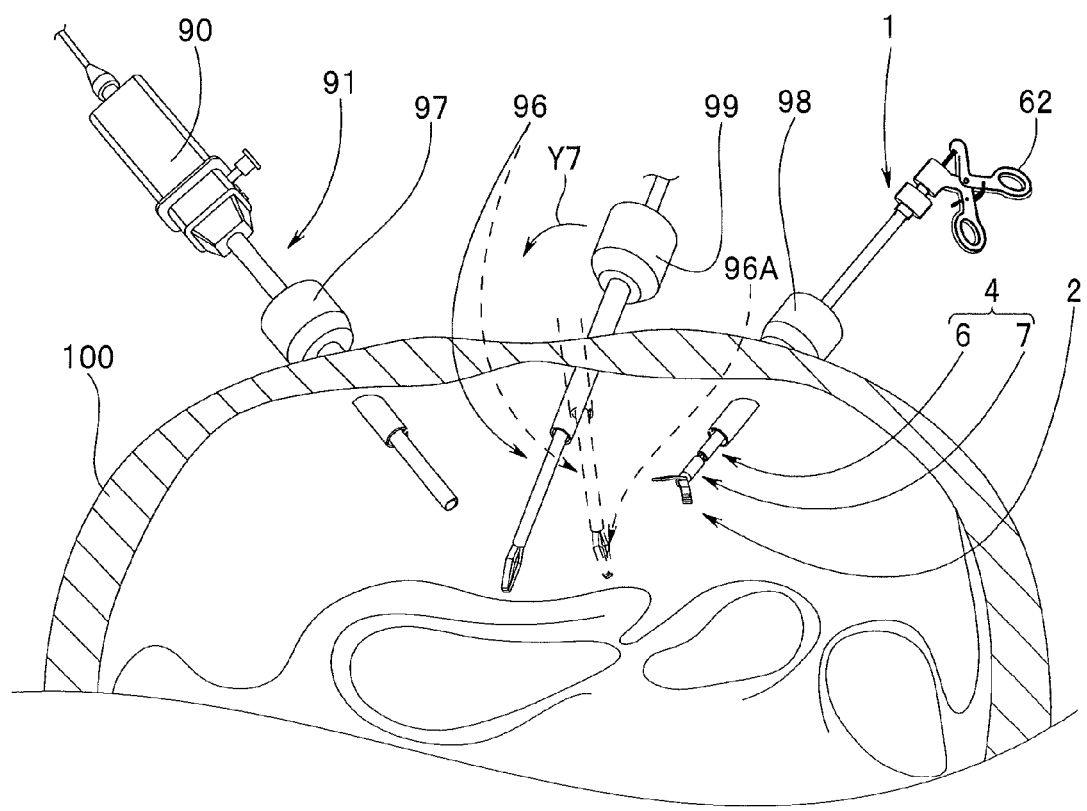
FIG. 7 relates to a view illustrating one operation example in which an operating surgeon manipulates the intra-abdominal cavity operation supporting forceps operated by an assistant and illustrating a state where the operating surgeon indicates a tissue to be grasped to the assistant using a grasping portion of a grasping forceps operated by the operating surgeon himself/herself.

Note that, when the intra-abdominal surgery is performed, four trocars are punctured into the abdominal wall 100, for example. As shown in FIGS. 6 and 7, the first trocar 97 is used for inserting the rigid endoscope 91 into the abdominal cavity, the second trocar 98 is used for inserting the surgical forceps 1 into the abdominal cavity, the third trocar 99 is used for inserting the grasping forceps 96 handled by the operating surgeon into the abdominal cavity, and the fourth trocar not shown is used for inserting the electrocautery scalpel into the abdominal cavity.

The surgical forceps 1 according to the present embodiment is configured to be usable by an experienced assistant and an inexperienced assistant.

First, description will be made on a case where an experienced assistant uses the surgical forceps 1.

In this case, the surgical forceps 1 is configured such that the insertion portion 4 functions as a rigid grasping forceps. Specifically, the joint portion 8 of the surgical forceps 1 is held in the linear state in which the central axis 10a of the opening/closing operation portion main body 10 and the central axis 40a of the insertion portion external body 40 coincide with each other, as shown by the solid lines in FIG. 4. That is, when using the surgical forceps 1, the experienced assistant moves the joint fixing knob 44 to the distal end side of the insertion portion external body 40, to press the spherical portion 17 to the distal-end through hole 45 by the pressing surface 54 of the fixing rod 50, and sets the insertion portion main body 6 and the distal-end-side constituting portion 7 of the insertion portion 4 in a linear state.

According to the surgical forceps 1, the assistant performs operation for moving the movable handle 62 in the arrow Y2c direction in FIG. 2, thereby moving the operation rod main body 33 and the wire 30 in the arrow Y2e direction, and can perform closing operation for respectively moving the grasping members 21, 22 of the grasping portion 2 in the directions shown by the arrows Y2b. In addition, the surgical forceps 1 is provided with the ratchet mechanism, which prevents the grasping members 21, 22 closed by the movement of the movable handle 62 from moving in an open direction.

On the other hand, the assistant moves the operation portion 64a of the ratchet release lever 64 in the arrow Y2f direction, thereby moving the movable handle 62 in the direction opposite to the arrow Y2c direction and can perform operation for bringing the grasping members 21, 22 into an open state.

That is, the experienced assistant supports the proceeding of the medical procedure such as pulling of a tissue, by appropriately operating at hand the surgical forceps 1 including the insertion portion 4 in the state where the insertion portion main body 6 and the distal-end-side constituting portion 7 are in the linear state, in accordance with the instruction by the operating surgeon.

Next, with reference to FIGS. 7 to 11, description will be made on an operation example in which the operating surgeon manipulates the surgical forceps operated by an inexperienced assistant.

When the inexperienced assistant handles the surgical forceps 1, the assistant first brings the insertion portion main body 6 and the distal-end-side constituting portion 7 of the insertion portion 4 into the linear state similarly as described above. In addition, the assistant sets, in advance, the grasping members 21, 22 in an introduceable closed state so that the grasping portion 2 of the surgical forceps 1 smoothly passes through an introduction hole of the second trocar 98.

When receiving an instruction for inserting the surgical forceps 1 into a body cavity from the operating surgeon, the assistant inserts the grasping portion 2 of the surgical forceps 1 into the body cavity through the trocar 98. After that, the assistant operates the ratchet release lever 64 and the movable handle 62 while checking the endoscopic image on the second display apparatus 95, to set the grasping members 21, 22 of the grasping portion 2 inserted into the body cavity in the open state as coached in advance, as shown in FIG. 7. Then, the assistant waits for an instruction from the operating surgeon.

Note that the open state of the grasping portion 2 is held by the ratchet mechanism.

The operating surgeon gives a verbal instruction to the assistant to bring the grasping portion 2 close to a tissue. In addition, as shown in FIG. 7, the operating surgeon changes the orientation of the trocar 99 as shown by the arrow Y7, with the puncturing point of the abdominal wall 100 as a center, and indicates a region to be grasped using a grasping portion 96A of the grasping forceps 96 which is inserted into the body cavity and operated by the operating surgeon himself/herself, as shown by dashed lines. During this process, the assistant confirms the region to be grasped while viewing the endoscopic image on the second display apparatus 95.

After that, the operating surgeon instructs the assistant to grasp the tissue. If the assistant requests another explanation, or the operation performed by the assistant is not the operation desired by the operating surgeon, the operating surgeon changes the instruction. That is, the operating surgeon tells the assistant to stop the grasping of the tissue, and after that, instructs the assistant to relax the fingers and arms grasping the operation portion 5 and hold the surgical forceps 1.

Figure 8:
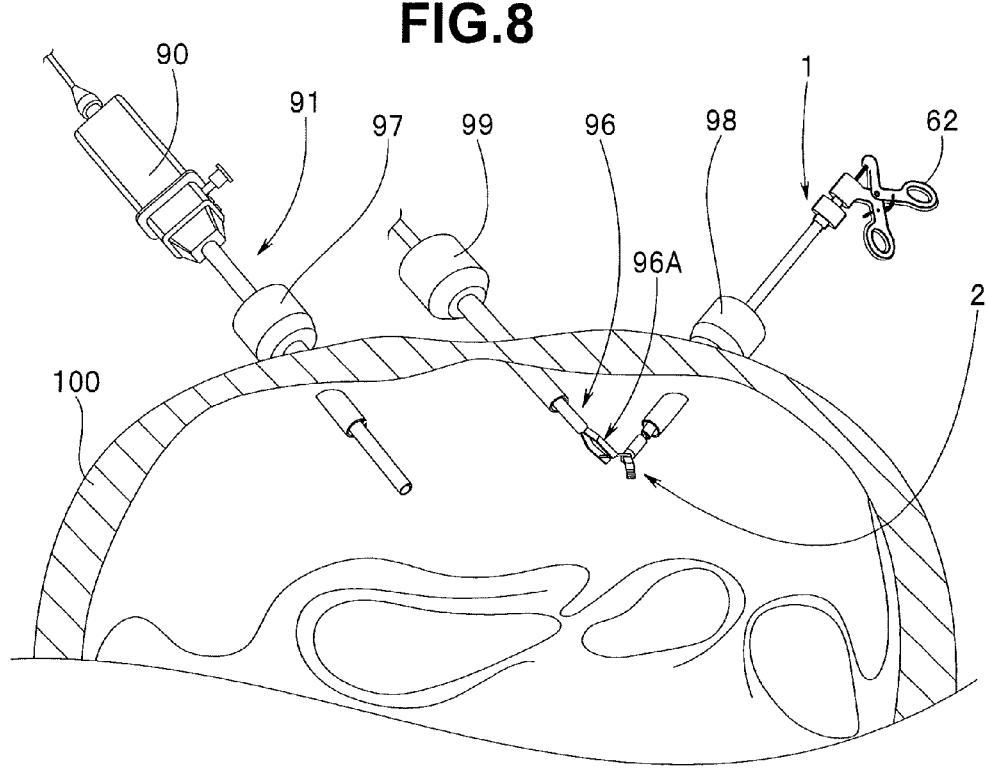
FIG. 8 relates to the one operation example in which the operating surgeon manipulates the intra-abdominal cavity operation supporting forceps operated by the assistant, and is a view illustrating a state where the operating surgeon grasps a predetermined part of the intra-abdominal cavity operation supporting forceps operated by the assistant, by using the grasping portion of the grasping forceps operated by the operating surgeon himself/herself.
Figure 9:
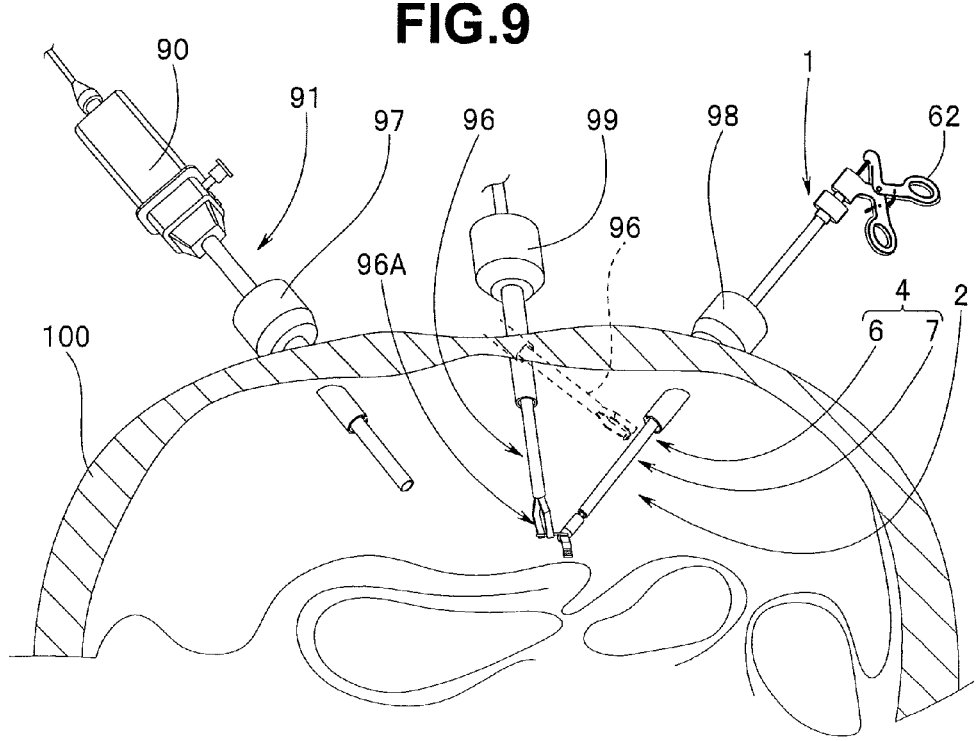
FIG. 9 relates to the one operation example in which the operating surgeon manipulates the intra-abdominal cavity operation supporting forceps operated by the assistant, and is a view illustrating a state where the operating surgeon causes the grasping portion of the intra-abdominal cavity operation supporting forceps operated by the assistant to face a tissue desired by the operating surgeon by using the grasping forceps operated by the operating surgeon himself/herself.

Next, the operating surgeon grasps any one of the projection pieces 11, the first grasping member 21 and the second grasping member 22 of the grasping portion 2, the insertion portion main body 6, and the like, by using the grasping portion 96A of the grasping forceps 96 operated by the operating surgeon himself/herself, as shown in FIG. 8. Then, the operating surgeon moves the grasping portion 96A of the grasping forceps 96 by operation at hand, to cause the grasping portion 2 to face a target region desired by the operating surgeon himself/herself, as shown in FIG. 9.

After that, the operating surgeon instructs the assistant to hold the state in which the grasping portion faces the target region. Then, the operating surgeon moves the grasping portion 96A of the grasping forceps 96 to the grasping portion opening/closing mechanism 16 to perform grasping operation to push the transmitting member 31 into the side hole 13.

Figure 10:
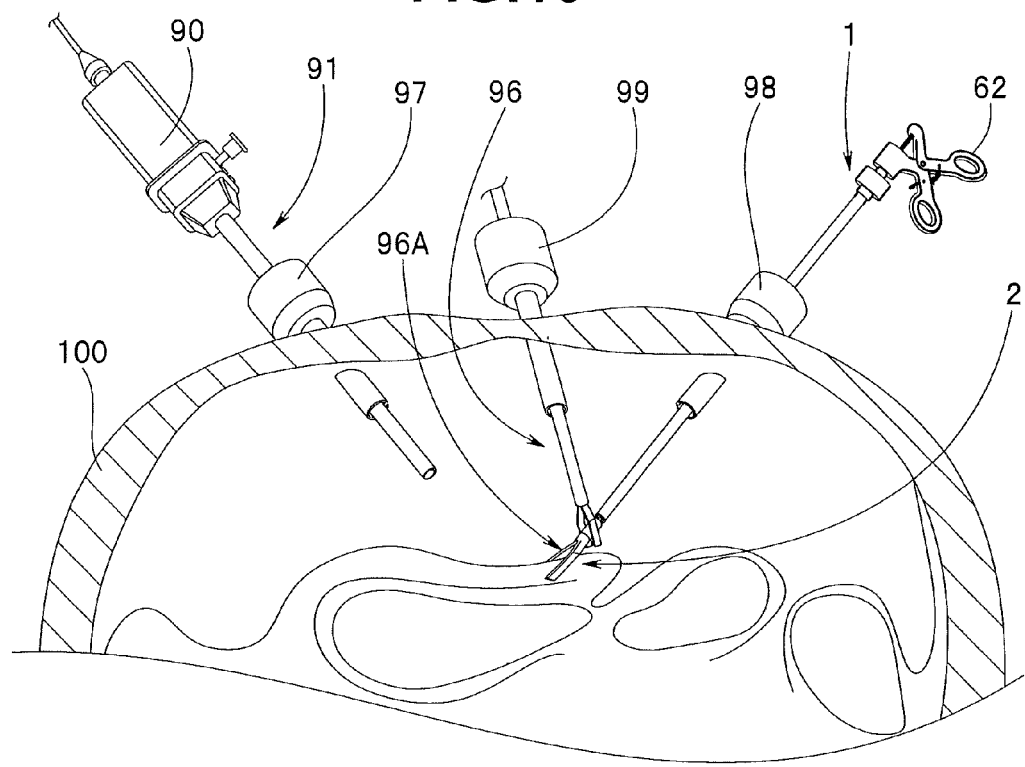
FIG. 10 relates to the one operation example in which the operating surgeon manipulates the intra-abdominal cavity operation supporting forceps operated by the assistant, and is a view illustrating a state where the operating surgeon manipulates an operation mechanism of the intra-abdominal cavity operation supporting forceps faced to the tissue to close grasping members of the grasping portion, thereby grasping the tissue.
Figure 11:
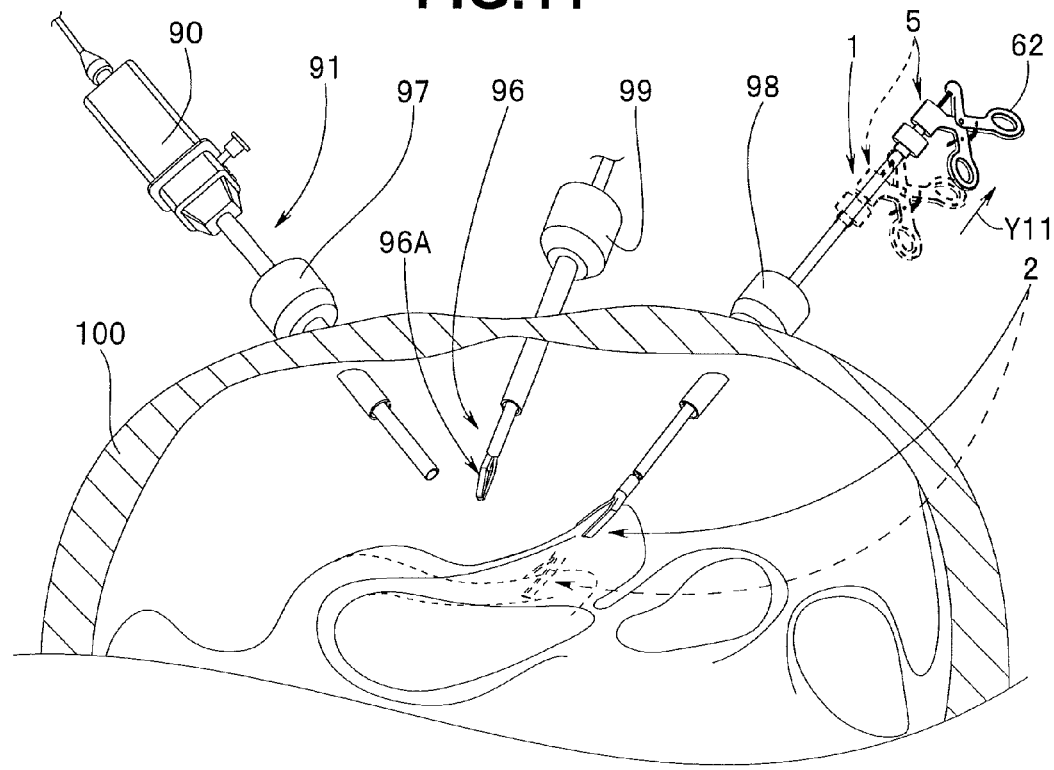
FIG. 11 relates to the one operation example in which the operating surgeon manipulates the intra-abdominal cavity operation supporting forceps operated by the assistant, and is a view illustrating a state where the operating surgeon pulls the tissue grasped by the grasping portion of the intra-abdominal cavity operation supporting forceps operated by the assistant.

Then, the grasping members 21, 22 in the open state are gradually closed against the biasing force of the pushing spring 29 without the movable handle 62 being operated, and the tissue is grasped by the first grasping member 21 and the second grasping member 22 as shown in FIG. 10.

During this process, the assistant confirms or figures out the moving operation method, the grasping operation method and the position desired by the operating surgeon based on the endoscopic image displayed on the second display apparatus 95, sensation transmitted to his or her fingers, and the like.

After that, the operating surgeon instructs to the assistant to increase the amount of force for grasping the tissue. Upon receiving the instruction, the assistant operates the movable handle 62 to increase the amount of grasping force applied to the tissue by the grasping members 21, 22 and surely grasps the tissue. After that, in accordance with the instruction by the operating surgeon, the assistant performs operation to pull the operation portion 5 back to his or her hand side as shown by the arrow Y11 in FIG. 11, to pull the tissue grasped by the grasping portion 2. Then, the grasping portion 2 grasping the tissue as shown by the dashed lines moves as shown by the solid lines, and the tissue is pulled. The operating surgeon then obtains a desired pulling state and performs dissection and the like using the electrocautery scalpel.

Next, with reference to FIGS. 12 to 18, description will be made on another operation example in which the operating surgeon manipulates the surgical forceps operated by the assistant.

Figure 12:
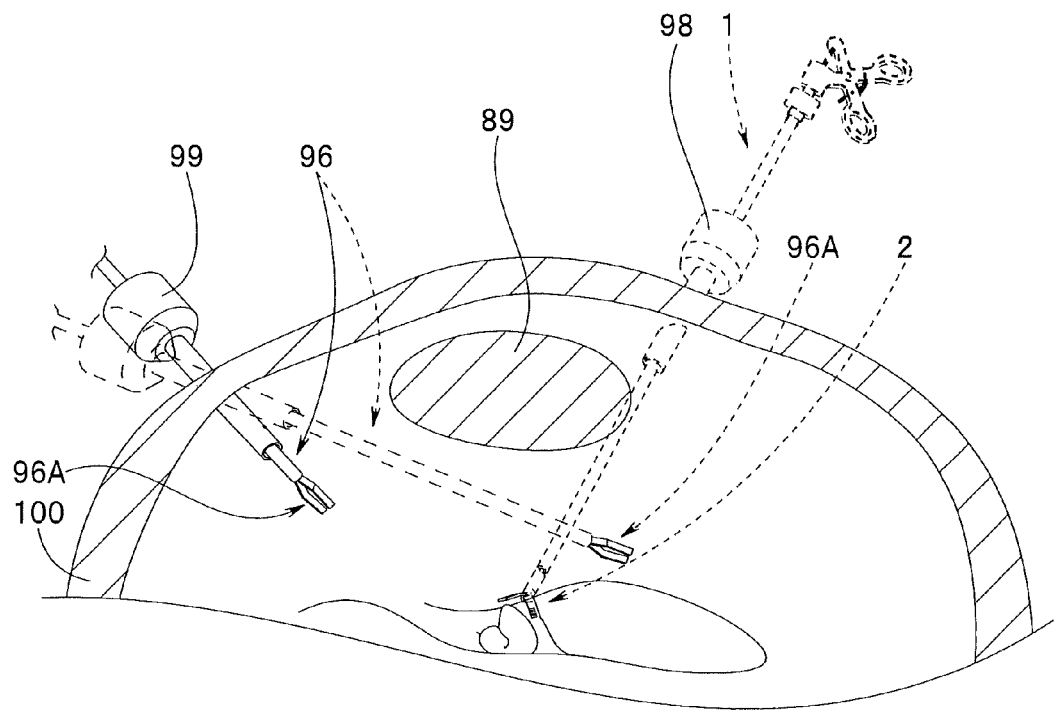
FIG. 12 relates to another operation example in which the operating surgeon manipulates the intra-abdominal operation supporting forceps operated by the assistant, and is a view illustrating a state where, when an obstacle is present in an advancing direction of the intra-abdominal cavity operation supporting forceps to be projected from a trocar, the operating surgeon indicates to the assistant a projection direction of the intra-abdominal cavity operation supporting forceps by using the grasping portion of the grasping forceps operated by the operating surgeon himself/herself.

In a laparoscopic surgery, if the trocar 98 is punctured into the abdominal wall 100 as shown by the dashed lines in FIG. 12, there is a case where internal organs or bones stand in the way of the grasping portion 2 of the surgical forceps 1 as an obstacle 89. In such a case, even if the assistant has a lot of experiences, it is difficult to grasp the operating surgeon's intended region.

The operating surgeon uses the surgical forceps 1 according to the present embodiment and performs the surgery cooperatively with an experienced assistant, as shown below.

The operating surgeon considers whether or not the internal organs or the bones could be the obstacle 89 which stands in the way of the surgical forceps 1, based on the endoscopic image on the first display apparatus 94. When determining that the internal organs and the like could be the obstacle 89, the operating surgeon gives a verbal instruction to the assistant to change the insertion direction of the grasping portion 2 of the surgical forceps 1 due to the presence of the obstacle 89.

The operating surgeon changes the orientation of the trocar 99 as shown in FIG. 12, and locates the grasping portion 96A of the grasping forceps 96 operated by the operating surgeon himself/herself at a desired position as a landmark as shown by the dashed lines. After that, the operating surgeon gives an instruction to the assistant to move the grasping portion 2 toward the grasping portion 96A.

Figure 13:
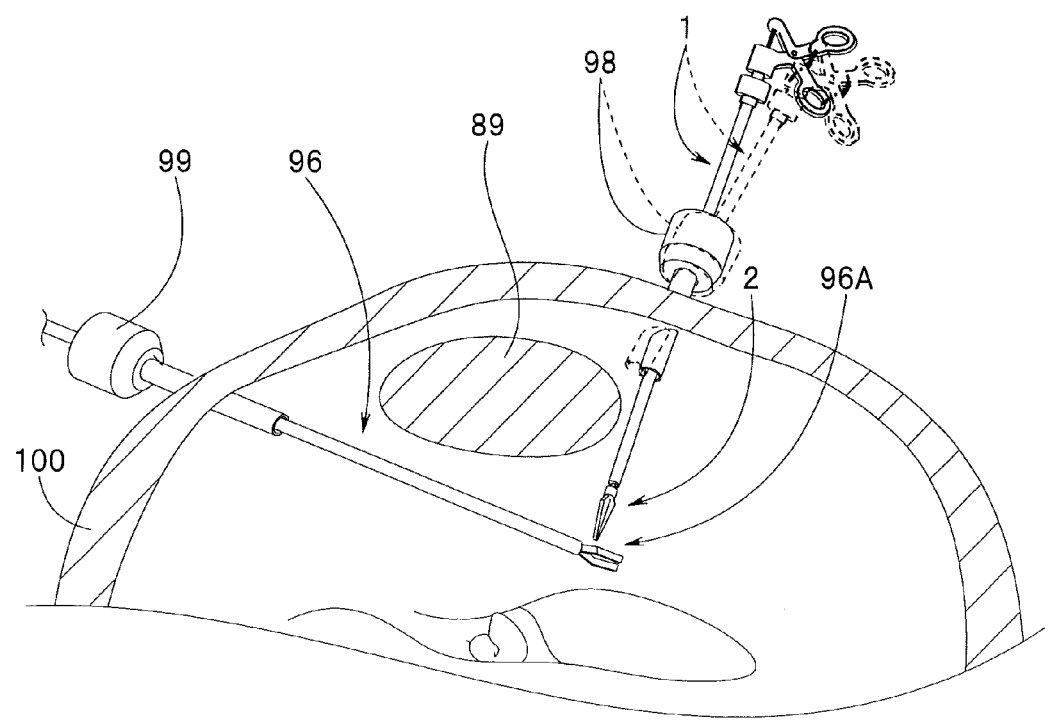
FIG. 13 relates to the other example in which the operating surgeon manipulates the intra-abdominal cavity operation supporting forceps operated by the assistant, and is a view illustrating a state where the assistant moves the intra-abdominal cavity operation supporting forceps toward a point indicated by the operating surgeon.

As shown in FIG. 13, the assistant first performs operation at hand for changing the orientation of the trocar 98, with the puncturing point of the abdominal wall 100 as a center. After that, the assistant advances the grasping portion 2, which is protruded into the body cavity from the trocar 98, toward the grasping portion 96A, without bringing the grasping portion 2 into an open state, while checking the endoscopic image on the second display apparatus 95.

The operating surgeon checks the positions of the grasping portion 2 and the insertion portion 4 of the surgical forceps 1 operated by the assistant, based on the endoscopic image on the first display apparatus 94. Then, the operating surgeon gives a verbal instruction, and moves the grasping portion 96A of the grasping forceps 96 operated by the operating surgeon himself/herself, to locate the grasping portion 2 at the grasping position of the tissue desired by the operating surgeon himself/herself.

Figure 14:
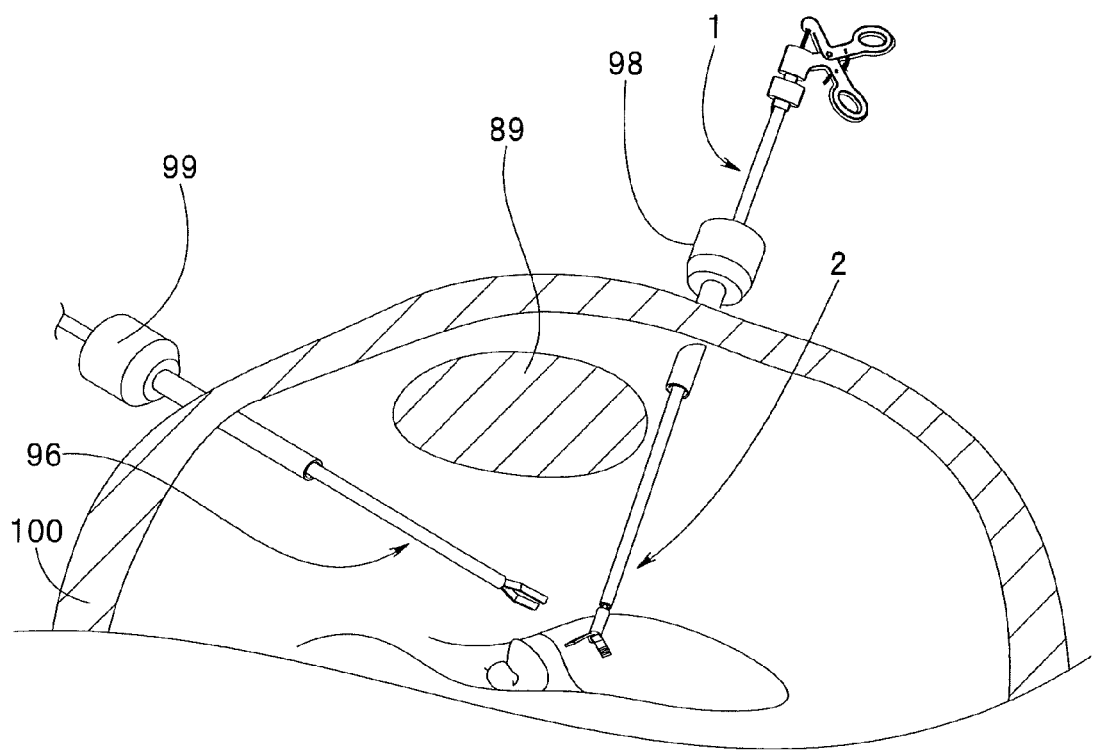
FIG. 14 relates to the other operation example in which the operating surgeon manipulates the intra-abdominal cavity operation supporting forceps operated by the assistant, and is a view illustrating a state where the assistant opens the grasping portion of the intra-abdominal cavity operation supporting forceps arranged at a tissue in the vicinity of the operating surgeon's desired grasping position.

After determining the grasping position, the operating surgeon gives an instruction to the assistant to bring the grasping members 21, 22 of the grasping portion 2 into an open state. Then, the grasping members 21, 22 of the grasping portion 2 are brought into the open state and arranged in the vicinity of the tissue to be grasped, as shown in FIG. 14.

Figure 15:
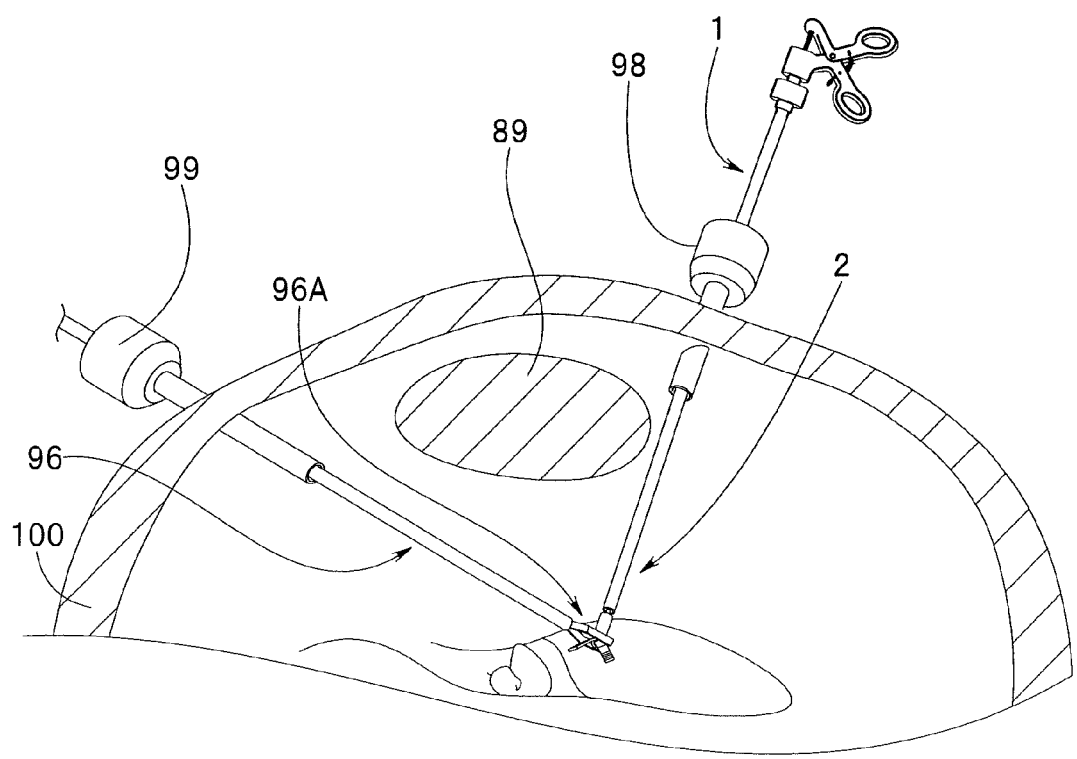
FIG. 15 relates to the other operation example in which the operating surgeon manipulates the intra-abdominal cavity operation supporting forceps operated by the assistant, and is a view illustrating an operation of moving the grasping portion in an open state so as to face the operating surgeon's desired grasping position of the tissue by using the grasping portion of the grasping forceps operated by the operating surgeon himself/herself.

Next, the operating surgeon gives the assistant an instruction to bring the joint portion 8 into a flexible state, that is, an instruction to loose the joint fixing knob 44. At this time, the operating surgeon grasps any one of the projection pieces 11, the first grasping member 21 and the second grasping member 22 of the grasping portion 2, the insertion portion main body 6, and the like, with the grasping portion 96A of the grasping forceps 96 operated by the operating surgeon himself/herself as shown in FIG. 15. In addition, the operating surgeon gives an instruction to the assistant to relax the hand and fingers grasping the operation portion 5 and strength of the hand, to hold the surgical forceps 1.

Figure 16:
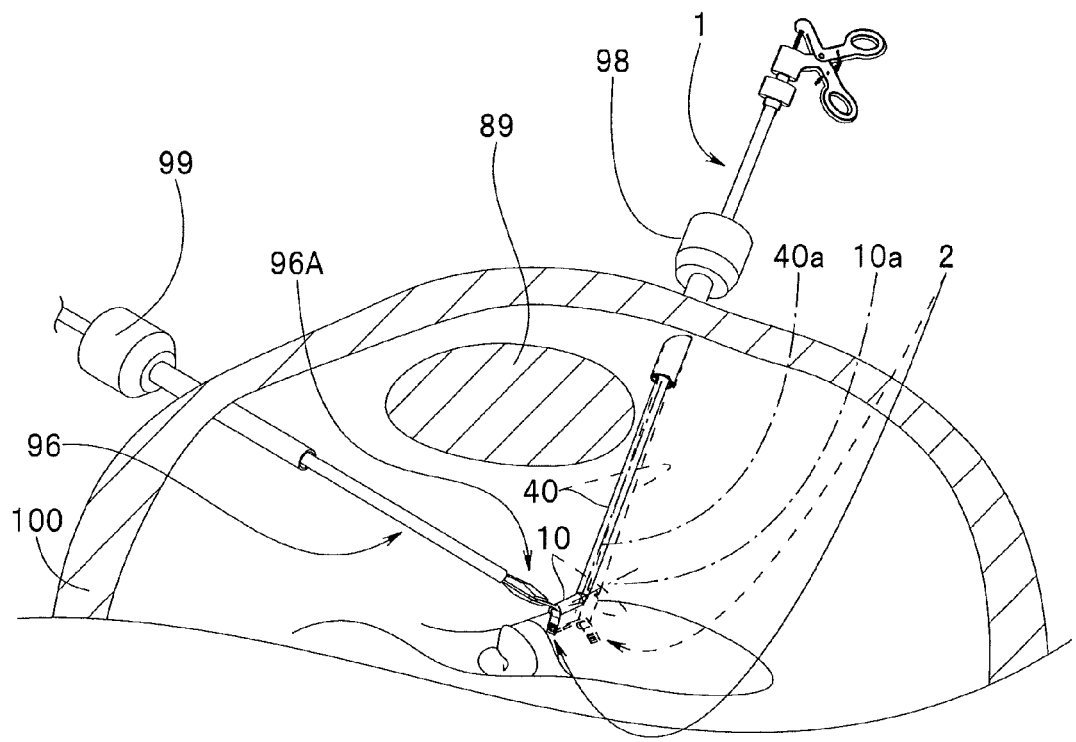
FIG. 16 relates to the other operation example in which the operating surgeon manipulates the intra-abdominal cavity operation supporting forceps operated by the assistant, and is a view illustrating a state where the grasping portion in the open state is faced to the operating surgeon's desired grasping position of the tissue.

After that, the operating surgeon operates, at hand, the grasping forceps 96 operated by the operating surgeon himself/herself and repeatedly gives instructions to move or revolve and operate the grasping portion 2 and to temporarily fix the joint portion 8. Then, the operating surgeon makes the grasping portion 2 face a target region desired by the operating surgeon himself/herself as shown in FIG. 16. When the joint portion 8 of the surgical forceps 1 is flexed and arranged in the vicinity of the tissue, the joint portion 8 is changed into the flexed state in which the central axis 10a of the opening/closing operation portion main body 10 and the central axis 40a of the insertion portion external body 40, which were in the linear state as shown by the dashed lines, intersect with each other.

Figure 17:
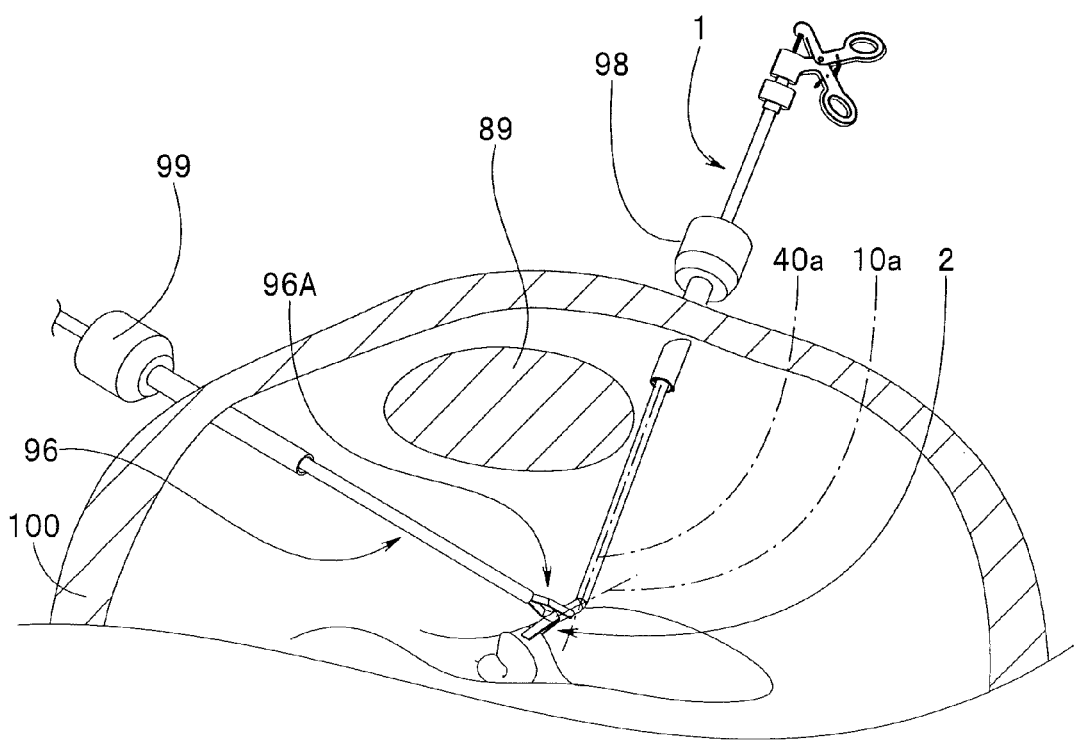
FIG. 17 relates to the other operation example in which the operating surgeon manipulates the intra-abdominal cavity operation supporting forceps operated by the assistant, and is a view illustrating a state where the operating surgeon manipulates the operation mechanism of the intra-abdominal cavity operation supporting forceps faced to the tissue to close the grasping members of the grasping portion, thereby grasping the tissue.

Next, the operating surgeon gives the assistant an instruction to fix the joint portion 8, that is, an instruction to tighten up the joint fixing knob 44. Then, after checking the fixing of the joint portion 8, the operating surgeon moves the grasping portion 96A of the grasping forceps 96 to the grasping portion opening/closing mechanism 16 and performs grasping operation to push the transmitting member 31 into the side hole 13 by using the grasping portion 96A. The grasping members 21, 22, which were in the open state, are then gradually closed, and the tissue is grasped by the first grasping member 21 and the second grasping member 22, as shown in FIG. 17.

After that, the operating surgeon gives an instruction to the assistant to increase an amount of force for grasping the tissue. Upon receiving the instruction, the assistant operates the movable handle 62 to increase the amount of force for grasping the tissue by the grasping members 21, 22 and surely grasps the tissue.

Figure 18:
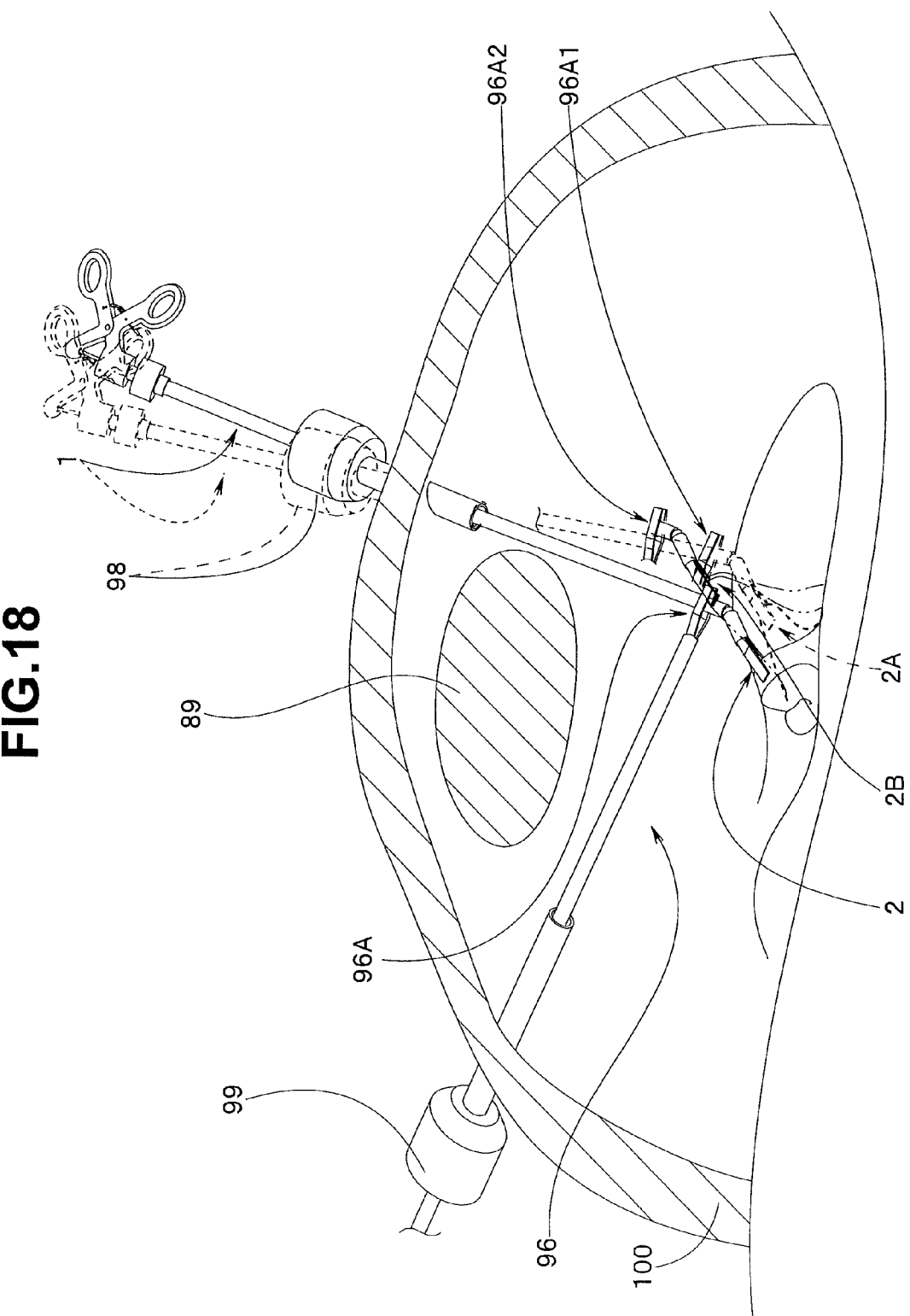
FIG. 18 relates to the other operation example in which the operating surgeon manipulates the intra-abdominal cavity operation supporting forceps operated by the assistant, and is a view illustrating a state where the operating surgeon operates his or her grasping forceps and gives guidance about the actual movement of the forceps to the assistant in order to explain a procedure of pulling the tissue and a desired pulling state.

Next, the operating surgeon again grasps the insertion portion external body 40 of the surgical forceps 1, for example, with the grasping portion of the grasping forceps operated by the operating surgeon himself/herself, as shown in FIG. 18. After that, the operating surgeon teaches the assistant the procedure of pulling operation. The operating surgeon performs operation to move the grasping portion 96A of the grasping forceps 96 to a position 96A1 first and then to a position 96A2, for example, as shown in FIG. 18 and gives a verbal instruction, while observing the endoscopic image on the first display apparatus 94. At this time, the grasping portion 2 of the surgical forceps 1 is moved to a position 2A first and then to a position 2B, in accordance with the movement of the grasping portion 96A to the positions 96A1 and 96A2, thereby enabling the tissue to be pulled in a desired state.

While the operating surgeon moves the grasping portion 2 of the surgical forceps 1, the assistant figures out the pulling procedure and the pulling state desired by the operating surgeon from the endoscopic image displayed on the second display apparatus 95, the sensation transmitted to the hand and fingers, and the change in the inclination of the trocar 98 protruded from the abdominal wall.

After that, the operating surgeon gives the assistant an instruction to pull the tissue. The assistant pulls and holds the tissue by operating the surgical forceps 1 so as to be able to obtain the pulling state as previously taught. The operating surgeon continues the medical procedure while giving instructions to the assistant. Even after that, the operating surgeon carries on the medical procedure cooperatively with the assistant while giving a demonstration of moving the grasping portion 2 of the surgical forceps 1 as described above or giving instructions to the assistant.

Note that, in the present embodiment, when teaching the pulling procedure of a tissue and the desired pulling state, the operating surgeon gives a demonstration of moving the grasping portion 2 of the surgical forceps 1 to the position 2A first and then to the position 2B, with the joint portion 8 held in a flexed state. However, the operating surgeon may give the demonstration of moving the grasping portion 2 of the surgical forceps 1, with the above-described joint portion 8 in the linear state, and may teach the pulling procedure of the tissue and the desired pulling state. In addition, when extracting the surgical forceps 1 from the trocar 98, the operating surgeon gives an instruction to release the flexed state of the joint portion 8 beforehand.

According to the surgical forceps of the present embodiment, the grasping portion opening/closing operation portion, which can be manipulated by the grasping forceps or the like operated by the operating surgeon, is provided in the vicinity of the grasping portion. As a result, during a surgery, the operating surgeon uses the grasping forceps operated by himself/herself to actually change the state of the grasping portion of the surgical forceps operated by the assistant into a grasping state instead of the operation at hand by the assistant.

According to the surgical forceps provided with the grasping portion opening/closing operation portion, when teaching the operation for actually grasping the tissue with the grasping forceps of the assistant during the medical procedure, the operating surgeon can carry on the medical procedure without moving toward the side of the assistant.

In addition, the operation portion of the surgical forceps is provided with the rack portion having the teeth portion configuring the ratchet mechanism and the ratchet release lever having the pawl portion configuring the ratchet mechanism. As a result, it is possible to grasp the tissue by operating the movable handle of the operation portion and hold the state where the tissue is grasped.

According to the surgical forceps including the operation portion having the ratchet mechanism, it is possible to increase the amount of force for grasping the tissue by the operation at hand by the assistant. In addition, when performing the pulling operation, the assistant can concentrate on the work of pulling the surgical forceps without paying any attention to adjustment of the amount of force for grasping the handle of the surgical forceps.

Furthermore, the surgical forceps according to the present embodiment includes, in addition to the grasping portion opening/closing operation portion and the ratchet mechanism, the insertion portion configured by the insertion portion main body and distal-end-side constituting portion, and the joint portion for connecting the insertion portion main body and the distal-end-side constituting portion in a flexible manner. In addition, the joint portion is held in a flexible state, in the flexed state, and in the linear state, by advancing or retracting the fixing rod by operating the joint fixing knob provided at the insertion portion.

As a result, when the joint portion is held in the linear state, an experienced assistant can use the surgical forceps as a grasping forceps. In addition, during the surgery, the operating surgeon can appropriately flex the joint portion of the surgical forceps which is inserted into the body cavity and operated by the assistant, to make the grasping portion of the surgical forceps face the tissue, and also can grasp the tissue by the grasping portion, by using the grasping forceps operated by himself/herself. According to the surgical forceps provided with the grasping portion opening/closing operation portion and the joint portion, the operating surgeon appropriately sets the flex angle of the joint portion during the medical procedure, thereby capable of realizing the best pulling operation and performing treatments and the like.

Figure 19:
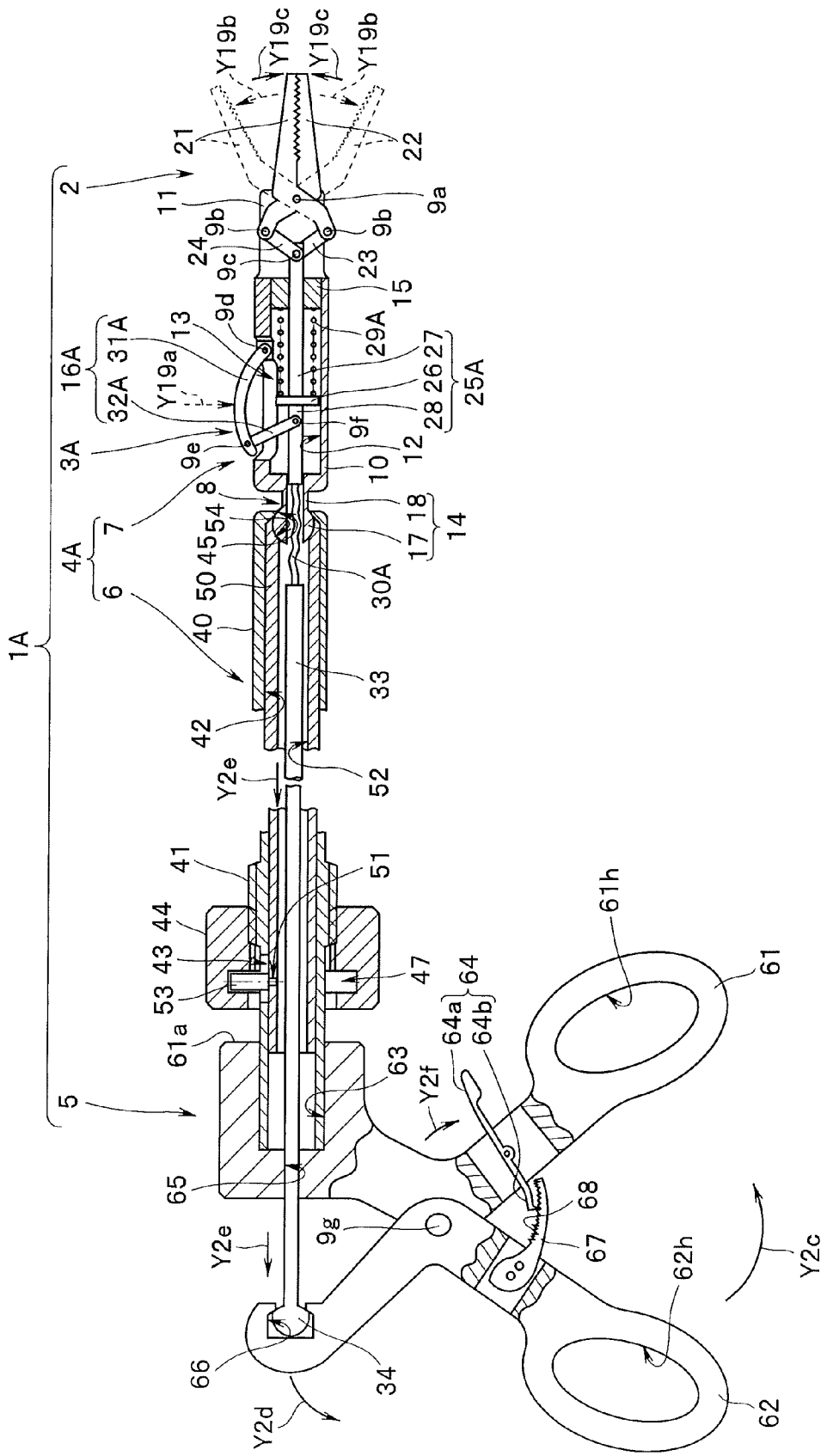
FIG. 19 is a view illustrating another configuration of the intra-abdominal cavity operation supporting forceps.
Figure 20:
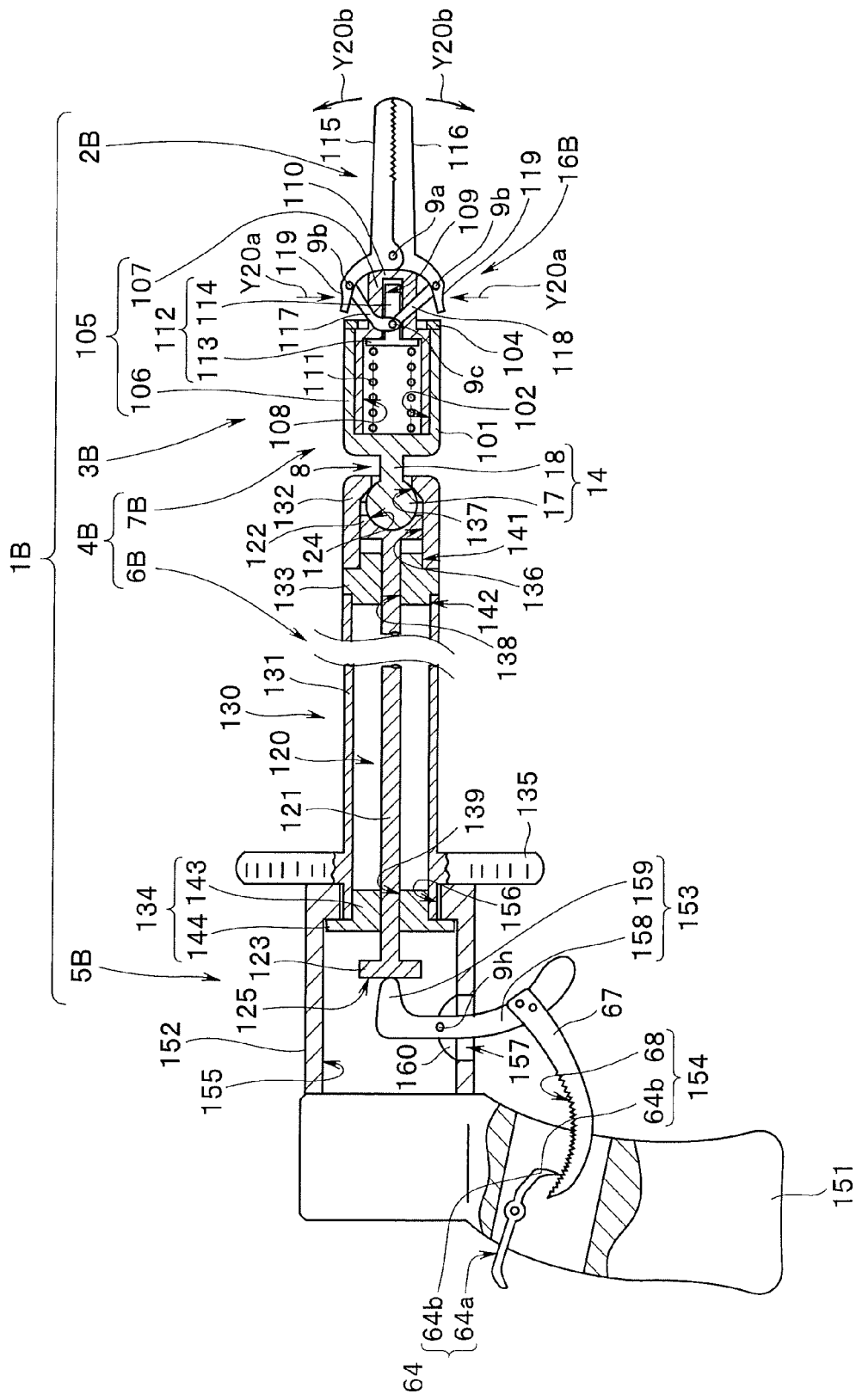
FIG. 20 is a view illustrating yet another configuration of the intra-abdominal cavity operation supporting forceps.

With reference to FIGS. 19, 20, exemplary configurations of the surgical forceps are described.

FIG. 19 relates to another exemplary configuration of the surgical forceps. A surgical forceps 1A shown in FIG. 19 is configured by including in the following order from the distal end side: the grasping portion 2; a grasping portion opening/closing operation portion 3A; an insertion portion 4A; and the operation portion 5. The surgical forceps 1A according to the present embodiment is different from the abode-described surgical forceps 1 in the initial state of the grasping portion 2.

Specifically, the grasping members 21, 22 of the grasping portion 2 of the surgical forceps 1 are in the maximum open state in the initial state. In contrast, when the surgical forceps 1A according to the present embodiment is in the initial state, the grasping members 21, 22 are in a closed state. Therefore, in the surgical forceps 1A, the configuration of the grasping portion opening/closing operation portion 3A which constitutes the insertion portion 4A is different from that of the corresponding component in the surgical forceps 1.

The grasping portion opening/closing operation portion 3A of the surgical forceps 1A includes a grasping portion opening/closing mechanism 16A. The grasping portion opening/closing mechanism 16A includes a transmitting member 31A provided in the side hole 13, and a rod moving bar 32A. The grasping portion opening/closing mechanism 16A is configured to change the grasping members 21, 22 of the treatment portion 2 from the closed state shown by the solid lines to the open state shown by the dashed lines, by pushing the transmitting member 31A of the grasping portion opening/closing mechanism 16A into the side hole 13 as shown by the dashed line arrow Y19a in the drawing. When the pushing of the transmitting member 31A is released, the grasping members 21, 22 of the treatment portion 2 return to the original closed state by the biasing force of a pushing spring 29A.

The transmitting member 31A of the grasping portion opening/closing mechanism 16A is formed in a predetermined bending shape, for example. The transmitting member 31A is provided with a first through hole (not shown) through which a second fulcrum pin 9d is inserted, and the second through hole (not shown) through which the third rotation pin 9e is inserted.

The rod moving bar 32A is formed in a straight shape. The rod moving bar 32A includes a first through hole (not shown) through which the third pin 9e is inserted and a second through hole (not shown) through which the fourth rotation pin 9f is inserted.

In the present embodiment, one end portion of the transmitting member 31A is rotatably arranged on the distal end side in the side hole 13 by the second fulcrum pin 9d. The one end side of the rod moving bar 32A is rotatably connected to the other end side of the transmitting member 31A by the third rotation pin 9e. The other end side of the rod moving bar 32A is rotatably connected to the proximal end rod 28 of a first rod 25A by the fourth rotation pin 9f. In this connected state, the intersecting angle between the transmitting member 31A and the rod moving bar 32A is an acute angle.

Note that the first rod 25A includes the flange portion 26, a distal end rod 27 configuring the more distal end side than the flange portion 26, and the proximal end rod 28 configuring the more proximal end side than the flange portion 26. The flange portion 26 is provided so as to be separated from the distal end surface by a predetermined distance. In addition, the first rod 25A according to the present embodiment includes a through hole through which a fourth rotation pin 9f is inserted, at a predetermined position between the proximal end surface of the proximal end rod 28 and the flange portion 26.

In addition, the pushing spring 29A is arranged in the space 12 at a position between the flange portion 26 and the lid body 15. The pushing spring 29A has a biasing force for moving the flange portion 26 in the bottom surface direction of the space 12.

Accordingly, in the surgical forceps 1A, the grasping members 21, 22 of the grasping portion 2 are in the closed state shown by the solid lines in FIG. 19 in the initial state, by the biasing force of the pushing spring 29A. When an external force in the direction shown by the arrow 19a in the drawing acts on the transmitting member 31A configuring the grasping portion opening/closing mechanism 16A, the transmitting member 31A is rotated in the counterclockwise direction in the drawing around the second fulcrum pin 9d, which causes the transmitting member 31A to move toward inside the side hole 13.

In accordance with the rotation of the transmitting member 31A, the rod moving bar 32A rotates around the third rotation pin 9e, and as a result, the intersecting angle becomes smaller. Then, the first rod 25A advances with respect to the opening/closing operation portion main body 10 against the biasing force of the pushing spring 29A. In accordance with the advancing, the grasping members 21, 22 move respectively in the directions shown by the arrows Y19b to be in the open state shown by the dashed lines. After that, when the external force acted on the transmitting member 31A is canceled, the grasping members 21, 22 of the grasping portion 2 are respectively moved in the directions shown by the arrows Y19c by the biasing force of the pushing spring 29A to be brought into the closed state shown by the solid lines again.

Note that, in the present embodiment, a length dimension of a wire 30A is set in view of the moving amount of the first rod 25A toward the distal end side. As a result, the wire 30A comes loose when the grasping members 21, 22 of the grasping portion 2 are in the closed state, and becomes a substantially linear state when the grasping members 21, 22 are in the open state.

Note that other configurations of the surgical forceps 1A are the same as those of the surgical forceps 1. The same components are attached with the same reference numerals and the descriptions thereof will be omitted.

Thus, the surgical forceps 1A of the present embodiment impairs the function of opening the grasping members 21, 22 of the grasping portion 2 by the operation of the movable handle 62 by the assistant. However, after arranging the grasping portion 2 at a region desired by the operating surgeon himself/herself, the operating surgeon performs operation for bringing the grasping members 21, 22 into the open state and into the closed state without relying on the assistant to operate the movable handle 62, thereby enabling the grasping portion 2 to grasp the tissue.

Other working and effects are the same as those of the above-described surgical forceps 1.

FIG. 20 relates to yet another exemplary configuration of the surgical forceps. A surgical forceps 1B shown in FIG. 20 is configured by including in the following order from the distal end side: a grasping portion 2B; a grasping portion opening/closing operation portion 3B; an insertion portion 4B; and an operation portion 5B. The surgical forceps 1B according to the present embodiment is configured such that grasping members 115, 116 of the grasping portion 2B are in a closed state in the initial state, similarly as in the surgical forceps 1A.

The insertion portion 4B of the surgical forceps 1B includes an insertion portion main body 6B and a distal-end-side constituting portion 7B. Similarly as in the above-described embodiment, the insertion portion main body 6B and the distal-end-side constituting portion 7B are connected so as to be flexible through the joint portion 8.

First, description will be made on the configuration of the distal-end-side constituting portion 7B which configures the insertion portion 4B.

The distal-end-side constituting portion 7B is a cylindrical opening/closing operation portion main body 101 and is provided with the grasping portion 2B having the grasping portion opening/closing operation portion 3B.

The opening/closing operation portion main body 101 includes a space 102 and the proximal-end-side protrusion 14. The space 102 is a hole having a bottom surface which is formed centering around the central axis of the opening/closing operation portion main body 101. The opening of the space 102 is configured to be closed by a lid body 104 having a central through hole. A large diameter portion 106 of a supporting member 105 is arranged in the space 102.

The supporting member 105 includes the large diameter portion 106 and a small diameter portion 107. A first hole 108 is formed at the large diameter portion 106. A pushing spring 111 and a flange portion 113 of an opening/closing rod 112 are slidably arranged in the first hole 108. On the other hand, a second hole 109 is formed at the small diameter portion 107. A rod main body 114 of the opening/closing rod 112 is slidably arranged in the second hole 109. The rod main body 114 is an operation rod.

The small diameter portion 107 is provided with a pair of projection pieces 110. The first hole 108 and the second hole 109 are stepped holes formed with respect to the central axis of the supporting member 105.

The opening/closing rod 112 is configured such that the rod main body 114 is slidably arranged in the second hole 109 and the flange portion 113 is slidably arranged in the first hole 108. In addition, the pushing spring 111 is arranged in the first hole 108 and biases the proximal end surface of the flange portion 113. The rod main body 114 is biased by the pushing spring 111 in the bottom surface direction of the second hole 109.

Note that, in a state where the distal end surface of the flange portion 113 abuts the bottom surface of the first hole 108, a gap is formed between the distal end surface of the rod main body 114 and the bottom surface of the second hole 109.

The large diameter portion 106 of the supporting member 105 is arranged in the space 102, with the opening/closing rod 112 and the pushing spring 111 arranged in the first hole 108 and the second hole 109, respectively. The lid body 104 prevents the opening/closing rod 112 and the pushing spring 111 from falling off from the opening of the space 102.

The small diameter portion 107 protrudes further than the large diameter portion 106 by a predetermined length, and protrudes from the through hole of the lid body 104 by a predetermined amount. The first grasping member 115 and the second grasping member 116 which constitute the grasping portion 2B are disposed between the pair of projection pieces 110. In the present embodiment, the first grasping member 115 and the second grasping member 116 also serve as a grasping portion opening/closing mechanism 16B.

The proximal-end-side protrusion 14 is provided so as to protrude from the proximal end surface of the opening/closing operation portion main body 101. The proximal-end-side protrusion 14 includes the spherical portion 17 and the shaft portion 18 which constitute the joint portion 8.

Note that the opening/closing operation portion main body 101 and the lid body 104 in the present embodiment are formed of a rigid metal member or a resin member and integrally configured by adhesive bonding, soldering, welding, screwing, or the like.

The grasping portion 2B includes a pair of grasping members 115, 116, the first fulcrum pin 9a, a pair of first rotation pins 9b, a pair of rotation members 117, 118, the rod main body 114, and the second rotation pin 9c.

The grasping members 115, 116 are formed in a predetermined flexed shape. A receiving surface 119 is provided on each of the proximal end sides of the grasping member 115 and the grasping member 116. On the receiving surfaces 119, the grasping members configuring the grasping portion of the grasping forceps (not shown) operated by the operating surgeon, which is a treatment instrument for example, are arranged.

Each of the grasping members 115, 116 has a first through hole (not shown) through which the first fulcrum pin 9a is inserted, and a second through hole (not shown) through which each of the first rotation pins 9b is inserted. The respective first through holes are formed halfway positions separated from the respective end surfaces of the grasping members 115, 116, by a predetermined distance. On the other hand, the respective second through holes are formed at predetermined positions on the respective other end sides of the grasping members 115, 116.

Each of the rotation members 117, 118 has a first through hole (not shown) through which each of the first rotation pins 9b is inserted and a second through hole (not shown) through which the second rotation pin 9c is inserted. The respective first through holes are formed at predetermined positions on one end sides of the rotation members 117, 118. The respective second through holes are formed at predetermined positions on the other end sides of the rotation members 117, 118. The rod main body 114 includes a through hole (not shown) through which the second rotation pin 9c is inserted, at a predetermined position between the distal end surface of the rod main body and the flange portion 113.

The pair of grasping members 115, 116 is rotatably connected to each other by the first fulcrum pin 9a. The rotation member 117 has one end side rotatably connected to the other end side of the grasping member 115 by one of the first rotation pins 9b. The rotation member 118 has one end side rotatably connected to the other end side of the grasping member 116 by the other of the first rotation pins 9b.

The grasping members 115, 116 which constitute the grasping portion 2B are rotatably disposed at the pair of the projection pieces 110 by the first fulcrum pin 9a being fixedly provided to the pair of projection pieces 110 of the opening/closing operation portion main body 101. The other end side of the rotation member 117 and the other end side of the rotation member 118 are rotatably connected to the rod main body 114 by the second rotation pin 9c.

According to this configuration, the grasping members 115, 116 which constitute the grasping portion 2B open and close in accordance with advancing and retracting of the opening/closing rod 112.

Specifically, the pair of the grasping members 115, 116 of the grasping portion 2B is brought into a closed state by the opening/closing rod 112 being moved to the distal end side by the biasing force of the pushing spring 111. Furthermore, the pair of the grasping members 115, 116 is brought into an open state by the opening/closing rod 112 being moved to the proximal end side against the biasing force of the pushing spring 111.

In the present embodiment, the biasing force of the pushing spring 111 is set such that the flange portion 113 is brought into contact with the bottom surface of the first hole 108, thereby bringing the grasping members 115, 116 into the closed state, and when the pushing spring 111 is compressed by the operation at hand by the operator, the grasping members 115, 116 are brought into the open state.

In the present embodiment, the grasping portion opening/closing mechanism 16B is configured by the pair of grasping members 115, 116, the pair of rotation members 117, 118, and the rod main body 114. In addition, in the present embodiment, external forces in the directions shown by the arrows Y20a in the drawing respectively act on the receiving surfaces 119 of the grasping members 115, 116, thereby causing the pair of grasping members 115, 116 to rotate respectively in predetermined directions centering around the first fulcrum pin 9a, and as a result, the grasping members 115, 116 respectively move in the directions shown by the arrows Y20b to be changed into the open state.

At this time, the rotation members 117, 118 rotate around the first rotation pins 9b, respectively, in accordance with the rotation of the grasping members 115, 116, thereby causing the flange portion 113 of the opening/closing rod 112 to retract against the biasing force of the pushing spring 111.

When the external forces acting on the receiving surfaces 119 are canceled, the flange portion 113 is brought into contact with the bottom surface of the first hole 108 again by the biasing force of the pushing spring, thereby causing the grasping members 115, 116 to return to the closed state. That is, the grasping members 115, 116 of the grasping portion 2B in the present embodiment are configured to be brought into the closed state by the biasing force of the pushing spring 111.

Next, description will be made on the configuration of the insertion portion main body 6B constituting the insertion portion 4B.

The insertion portion main body 6B includes a fixing rod 120 which is advanceable/retractable in an elongated insertion portion external body 130.

The fixing rod 120 includes a rod main body 121, a distal end portion 122, and a proximal end portion 123. The distal end portion 122 has a diameter larger than the outer diameter of the rod main body 121, for example. The distal end portion 122 has on the distal end surface thereof a pressing surface 124 which presses the spherical portion 17. The proximal end portion 123 also has a diameter larger than the outer diameter of the rod main body 121, for example, and includes an abutting surface 125 at which an abutting portion 159 of a flex fixing lever 153 to be described later is arranged in an abutting manner.

Note that, in the present embodiment, the rod main body 121 and the distal end portion 122 are formed as separated bodies, or the rod main body 121 and the proximal end portion 123 are formed as separated bodies, for example. The rod main body 121 and the distal end portion 122 as separated bodies, or the rod main body 121 and the proximal end portion 123 as separated bodies are integrally fixed by screwing, adhesive bonding, soldering, welding, or the like.

The insertion portion external body 130 is configured by including an elongated tubular portion 131, a cylindrical distal-end constituting portion 132, a rod distal end holding portion 133, and a rod proximal end holding portion 134.

The tubular portion 131 has an insertion portion rotation knob 135 at a predetermined position on the proximal end side. The insertion portion rotation knob 135 is provided integrally to the tubular portion 131 so as to protrude therefrom. The insertion portion external body 130 is configured such that the tubular portion 131 rotates around the axis thereof by rotating the insertion portion rotation knob 135.

The distal-end constituting portion 132 includes a fixing rod space 136. The fixing rod space 136 is a hole having a bottom surface which is formed centering around the central axis of the distal-end constituting portion 132. The distal end portion 122 of the fixing rod 120 and the spherical portion 17 are housed in the fixing rod space 136. Therefore, at the distal end portion of the distal-end constituting portion 132, a through hole in the axial direction which communicates between the fixing rod space 136 and outside is formed to configure the joint portion 8. The opening on the bottom surface side of the fixing rod space 136, which is one opening of the through hole, is formed as a distal-end through hole 137 having a curved surface on which the spherical portion 17 is slidable, or an inclined surface with which the spherical portion 17 is brought into contact.

The rod distal end holding portion 133 is a columnar member, for example, and has a first axis-direction through hole 138 through which the rod main body 121 is inserted so as to be movable. The first axis-direction through hole 138 is formed centering around the central axis of the rod distal end holding portion 133. The rod distal end holding portion 133 has, on the distal end side thereof, a first step portion 141 to which the opening side of the distal-end constituting portion 132 is arranged in an outwardly-fitted manner, and has, on the proximal end side thereof, a second step portion 142 at which the distal end portion side of the tubular portion 131 is arranged. The tubular portion 131 is integrally fixed to the second step portion 142 by screwing, adhesive bonding, soldering, welding, or the like. The distal-end constituting portion 132 is integrally fixed to the first step portion 141 by screwing, adhesive bonding, soldering, welding, or the like. The rod distal end holding portion 133 also serves as a connecting member which connects the tubular portion 131 and the distal-end constituting portion 132.

The distal-end constituting portion 132 is fixed to the rod distal end holding portion 133 in the state where the spherical portion 17 and the distal end portion 122 of the fixing rod 120 are disposed in the fixing rod space 136. In this fixed state, the distal end portion 122 in the fixing rod space 136 is advanceable/retractable.

The rod proximal end holding portion 134 is a columnar member having a holding portion main body 143 and a flange 144. The rod proximal end holding portion 134 has a second axis-direction through hole 139 through which the rod main body 121 is inserted so as to be movable. The second axis-direction through hole 139 is formed centering around the central axis of the rod proximal end holding portion 134. The proximal end side of the tubular portion 131 is arranged in an outwardly-fitted manner to the holding portion main body 143 of the rod proximal end holding portion 134. The tubular portion 131 is integrally fixed to the holding portion main body 143 of the rod proximal end holding portion 134 by screwing, adhesive bonding, soldering, welding, or the like.

Then, the spherical portion 17 configuring the proximal-end-side protrusion 14 of the opening/closing operation portion main body 101 is arranged in the distal-end through hole 137 of the insertion portion external body 130. The opening/closing operation portion main body 101 is capable of revolving around the central axis of the insertion portion external body 130 and changes into a linear state in which the central axis of the opening/closing operation portion main body 101 and the central axis of the insertion portion external body 130 coincide with each other, or a flexed state in which the central axes intersect with each other.

In addition, in the state where the central axis of the opening/closing operation portion main body 101 and the central axis of the insertion portion external body 130 intersect with each other, the grasping portion 2B can be arranged in the region 46 shown in the above-described FIG. 5, that is, a position in the up, down, left or right direction, a position between the up direction and the right direction, a position between the down direction and the left direction, with the central axis of the insertion portion external body 130 as a center, similarly as in the above-described embodiment.

The operation portion 5B according to the present embodiment is configured by including an operation portion main body (hereinafter, referred to as a grip) 151, a cylindrical body 152, the flex fixing lever 153 which configure a holding mechanism, and a ratchet mechanism portion 154.

The operation portion 5B according to the present embodiment includes the flex fixing lever 153 which switches the joint portion 8 between a free state and a fixed state, in place of the movable handle 62 which opens and closes the grasping members 21, 22 of the grasping portion 2 which is provided to the operation portion 5 in the first embodiment.

The cylindrical body 152 is integrally fixed to the grip 151 by screwing, adhesive bonding, soldering, welding, or the like. The ratchet release lever 64 is rotatably attached at a predetermined position of the grip 151. The operation portion 64a is protruded from the proximal end surface of the grip 151.

The cylindrical body 152 includes a space portion 155, and communicating holes 156, 157 which communicate between the space portion 155 and outside. The first communicating hole 156 is formed centering around the central axis of the cylindrical body 152. In the first communicating hole 156, the tubular portion 131 of the insertion portion external body 130 is arranged. The second communicating hole 157 is formed on the outer circumferential surface of the cylindrical body 152. In the second communicating hole 157, a lever main body 158 of the flex fixing lever 153 is inserted.

The flex fixing lever 153 includes the lever main body 158 and the abutting portion 159.

A through hole through which a fulcrum pin 9h is inserted is formed at a predetermined position of the lever main body 158. The lever main body 158 is pivotally supported in a rotatable manner at a mounting portion 160 provided in the space portion 155.

On the other hand, the abutting portion 159 is configured to abut the abutting surface 125 provided to the proximal end portion 123 of the fixing rod 120. The rotatable lever main body 158 has the rack portion 67 having the teeth portion 68, which is fixedly arranged at a predetermined position.

The abutting portion 159 abuts the abutting surface 125 of the proximal end portion 123 by rotating the flex fixing lever 153. By further rotating the flex fixing lever 153 in the abutting state, the fixing rod 120 moves toward the distal end side. The fixing rod 120 moves toward the distal end side, thereby capable of causing the pressing surface 124 of the fixing rod 120 to abut the spherical portion 17 arranged in the distal-end through hole 137 of the insertion portion external body 130, and also capable of pressing the spherical portion 17. The pressing force from the pressing surface 124 which abuts the spherical portion 17 increases, thereby capable of holding the linear state in which the central axis of the opening/closing operation portion main body 101 and the central axis of the insertion portion external body 130 coincide with each other, or the flexed state in which the central axes intersect with each other.

At this time, the rack portion 67 which configures the ratchet mechanism moves in accordance with the movement of the lever main body 158, and the positional relationship between the pawl portion 64b and the teeth portion 68 is changed. When the movement of the lever main body 158 is stopped, the lever main body 158 is held at the moved position by the ratchet mechanism portion 154.

On the other hand, the engaging state between the pawl portion 64b and the teeth portion 68 is released by operating the operation portion 64a of the ratchet release lever 64, thereby capable of moving the lever main body 158 in a reverse direction. When the engaged state between the pawl portion 64b and the teeth portion 68 is released, holding of the linear state in which the central axis of the opening/closing operation portion main body 101 and the central axis of the insertion portion external body 130 coincide with each other, or holding of the flexed state in which the central axes intersect with each other is released.

Note that other configurations of the surgical forceps 1B are the same as those of the surgical forceps 1 and 1A. The same components are attached with the same reference numerals and descriptions thereof will be omitted.

Thus, the surgical forceps 1B of the present embodiment impair the function of opening and closing the grasping members 115, 116 of the grasping portion 2B by the assistant who grasps the surgical forceps 1B and the function of increasing the grasping force amount by the grasping members 115, 116. However, similarly as in the above-described embodiment, after the operating surgeon arranges the grasping portion 2B at a region desired by himself/herself, the operating surgeon performs operation for bringing the grasping members 115, 116 in the open state and in the closed state and enables the grasping portion 2B to grasp the tissue, without relying on the assistant to operate the movable handle 62.

Note that, in the present embodiment, the grasping force amount by the grasping members 115, 116 of the grasping portion 2B can be appropriately set by the biasing force of the pushing spring 111.

Other working and effects are the same as those of the above-described surgical forceps 1 and 1A.

In the above-described embodiment, the biasing force of the pushing spring 111 is appropriately set, thereby capable of adjusting the grasping force amount of the grasping members 115, 116. Therefore, as shown in FIG. 21, a plurality of distal-end-side constituting portions 7B1, 7B2, 7B3, etc., which have different grasping force amounts, are previously prepared and the distal-end-side constituting portions 7B1, 7B2, 7B3, etc., are configured to be attachable and detachable with respect to the insertion portion main body 6B.

According to this configuration, a distal end-side constituting portion, which has a grasping force amount optimal for a certain medical procedure such as grasping blood vessels or grasping tissues including nerves, is appropriately selected from the distal-end-side constituting portions 7B1, 7B2, 7B3, etc., and the selected distal-end-side constituting portion is attached to the insertion portion main body 6B, thereby capable of realizing the surgical forceps 1B optimal for the medical procedure.

Figure 21:
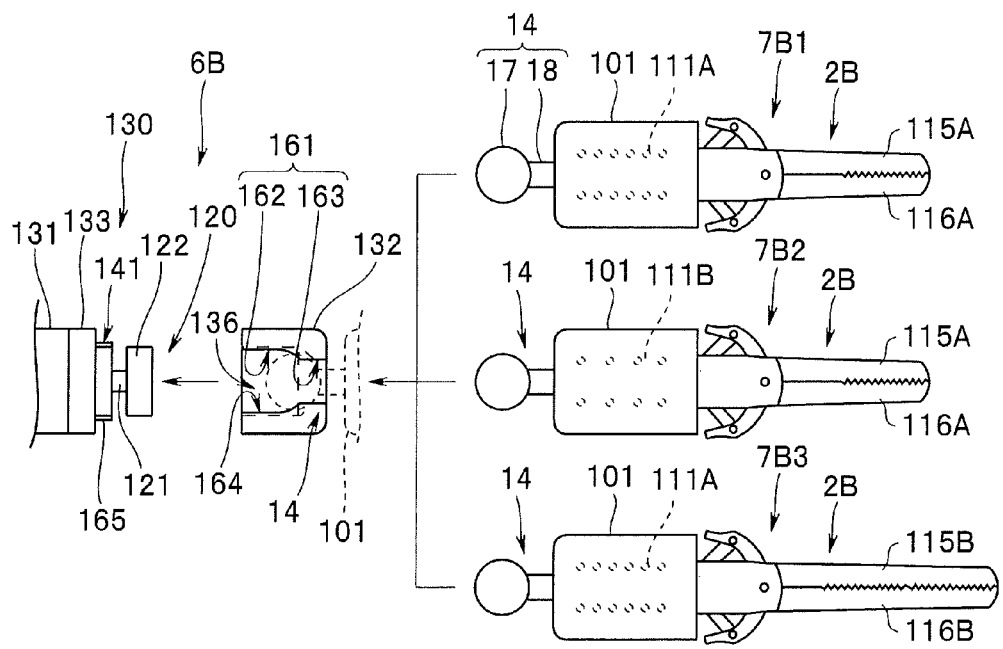
FIG. 21 is a view illustrating an exemplary configuration of the intra-abdominal cavity operation supporting forceps in which a plurality of kinds of distal-end-side constituting portions are attachable to and detachable from an insertion portion main body.

Note that the first distal-end-side constituting portion 7B 1, the second distal-end-side constituting portion 7B2, and the third distal-end-side constituting portion 7B3, which are shown in FIG. 21, are configured to have different grasping force amounts by using different pushing springs 111A, 111B, or configured such that the lengths, the widths and the like of the grasping surfaces of the pair of grasping members 115A, 116A are different from those of the pair of the grasping members 115B, 116B.

In addition, a notch groove 161 is provided to the distal-end constituting portion 132 for allowing the first distal-end-side constituting portion 7B1, the second distal-end-side constituting portion 7B2, and the third distal-end-side constituting portion 7B3, etc., which are the plurality of distal end-side constituting portions, to be detachably attached to the insertion portion main body 6B. In addition, the distal-end constituting portion 132 and the rod distal end holding portion 133 are attachable to and detachable from each other by screwing.

The notch groove 161 is formed on the side surface of the distal-end constituting portion 132 and communicates between the fixing rod space 136 and outside. The notch groove 161 includes a wide groove 162 through which the spherical portion 17 of the proximal-end-side protrusion 14 passes, and a narrow groove 163 through which the shaft portion 18 passes. A female screw 164 is formed on the inner surface of the fixing rod space 136. On the other hand, a male screw 165 which screws with the female screw 164 in the fixing rod space 136 is formed at the first step portion 141 of the rod distal end holding portion 133.

The length from the opening side end surface of the wide groove 162 to the narrow groove 163 is set to a dimension preventing the spherical portion 17 from falling off from the fixing rod space 136 when the distal-end constituting portion 132 is fixed to the rod distal end holding portion 133 by screwing.

In the above-described embodiment, the distal-end constituting portion 132 and the rod distal end holding portion 133 are configured to be attachable to and detachable from each other by screwing, and one of the distal-end-side constituting portions 7B1, 7B2, 7B3, etc., is configured to be attachable to and detachable from the insertion portion main body 6B. However, the attaching/detaching mechanism between the distal-end-side constituting portion 7B1, 7B2, 7B3, etc., and the insertion portion main body 6B is not limited to the attachment/detachment by screwing.

Figure 22:
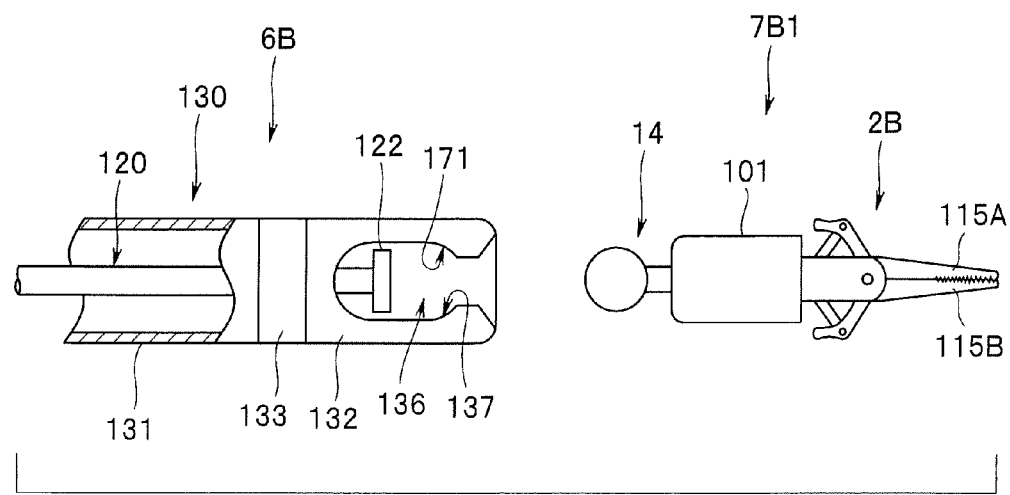
FIG. 22 is a view illustrating another configuration of the intra-abdominal cavity operation supporting forceps in which a plurality of kinds of distal-end-side constituting portions are attachable to and detachable from the insertion portion main body.

For example, in FIG. 22, a notch groove 171 through which the proximal-end-side protrusion 14 is insertable is formed on the side surface of the distal-end constituting portion 132, and the spherical portion 17 which is arranged in the fixing rod space 136 is pressed against the distal-end through hole 137 by the distal end portion 122 of the fixing rod 120 inserted in the insertion portion external body 130. According to this configuration, the distal-end-side constituting portion 7B1 and the like can be attachable to and detachable from the insertion portion main body 6B with a simple configuration in which the notch groove 171 is formed at the distal-end constituting portion 132.

Figure 23:
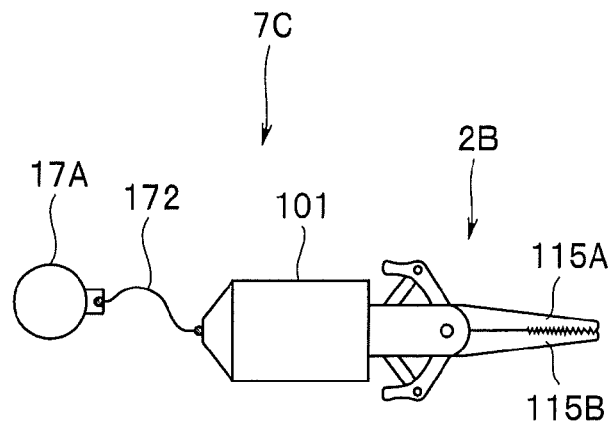
FIG. 23 is a view illustrating the distal-end-side constituting portion in which an opening/closing operation portion main body and a spherical portion are connected to each other by a wire.

Note that the opening/closing operation portion main body 101 and a spherical portion 17A may be connected by a wire 172 to configure the distal-end-side constituting portion 7C, as shown in FIG. 23. According to this configuration, when the hand of the assistant who operates the surgical forceps 1B erroneously moves in the direction in which the wire 172 is loosen during surgery, it is possible to prevent the grasping portion 2B from moving in accordance with the movement of the assistant's hand.

Figure 24:
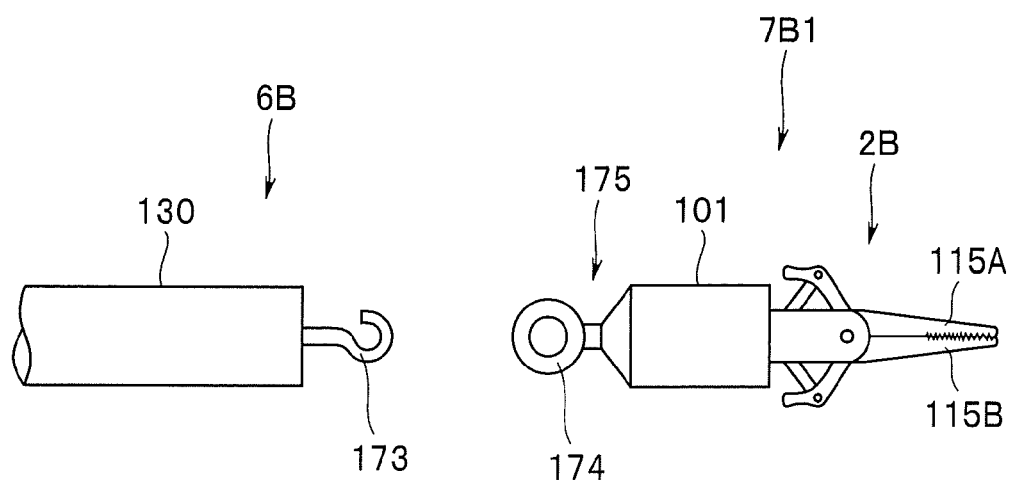
FIG. 24 is a view illustrating yet another example of the intra-abdominal cavity operation supporting forceps in which a plurality of kinds of distal-end-side constituting portions are attachable to and detachable from the insertion portion main body.

In addition, as shown in FIG. 24, a hook 173 protruding from the distal end of the insertion portion external body 130 may be provided and a ring member 175 having a ring 174 may be provided at the opening/closing operation portion main body 101 of the distal-end-side constituting portion 7B1 and the like. According to such a configuration, it is possible to more easily realize attaching/detaching between the distal-end-side constituting portion 7B1, etc., and the insertion portion main body 6B.

Note that the present invention is not limited only to the above-mentioned embodiments, but may be modified and embodied in various forms without departing from the scope of the present invention.

What is claimed is:

1. A surgical forceps comprising:
   an insertion portion main body including a distal end portion and a proximal end portion in a direction of a longitudinal axis;
   an opening/closing operation portion main body provided at the distal end portion of the insertion portion main body, and including an internal space formed along the longitudinal axis;
   a grasping portion provided to the opening/closing operation portion main body, and configured to grasp an object;
   a first operation portion provided at the proximal end portion of the insertion portion main body, and configured to operate a grasping movement of the grasping portion;
   an operation rod having one end portion and the other end portion and arranged in the internal space of the opening/closing operation portion main body so as to be movable along a direction of a longitudinal axis of the opening/closing operation portion main body, the one end portion being connected with the grasping portion so as to cause the grasping portion to perform grasping movement by the operation rod moving in the internal space according to operation of the first operation portion to which the other end portion is connected, wherein the opening/closing operation portion main body includes one side hole which communicates between the internal space and outside at a predetermined position on a side surface of the opening/closing operation portion main body, and a second operation portion is provided which includes a grasping portion opening/closing mechanism configured to be arranged in the one side hole, the grasping portion opening/closing mechanism causing the grasping portion to perform grasping movement by moving a distal-end-side operation rod configuring a part of the operation rod along a longitudinal direction of the opening/closing the operation portion main body.

2. The surgical forceps according to claim 1, wherein the grasping portion opening/closing mechanism configured to cause the grasping portion to perform grasping movement includes a first operation member and a second operation member provided in the one side hole and rotatably connected to each other, and an end portion of the first operation member which is not connected to the second operation member is rotatably connected to the side hole, and an end portion of the second operation member which is not connected to the first operation member is rotatably connected to the operation rod.

3. The surgical forceps according to claim 2, comprising:
a distal-end-side constituting portion provided on a distal end side of the insertion portion main body and including the second operation portion and the grasping portion, wherein the insertion portion main body and the distal-end-side constituting portion are connected to each other by a joint portion configured to be able to be bent or flexed, and a flexible member configuring a part of the operation rod is arranged so as to pass through a through hole formed at a protrusion which includes a spherical portion configuring the joint portion, the flexible member being able to be bent or flexed.

4. The surgical forceps according to claim 3, wherein the distal-end-side constituting portion includes a biasing member which biases the grasping portion in a direction in which the object is grasped by the grasping portion or in a direction in which the grasping is released.

5. The surgical forceps according to claim 4, wherein the grasping portion includes:
a pair of grasping members configured to be openable/closable, each of the pair of grasping members having a grasping surface for grasping a tissue on one end side;
a holding member arranged at a halfway portion of the pair of grasping members, for rotatably holding each of the pair of grasping members;
rotation members each having one end side which is rotatably connected to the other end side of each of the pair of grasping members; and the operation rod having one end side to which the other end side of each of the rotation members is rotatably connected, the operation rod being advanceable/retractable in an axis direction, and the second operation portion for switching the grasping members into an open state or a closed state, includes:
the opening/closing operation portion main body which is formed by a cylindrical body having the internal space in which the operation rod is slidably arranged; and
a biasing member arranged in the internal space of the opening/closing operation portion main body, the biasing member biasing the operation rod to move the operation rod in the axis direction and hold the grasping portion in an open state or in a closed state.

6. The surgical forceps according to claim 5, wherein the grasping portion includes a receiving surface provided at a proximal end portion of each of the pair of grasping members.

7. The surgical forceps according to claim 5, wherein the distal-end-side constituting portion and the insertion portion main body are connected to each other through a joint portion which allows the distal-end-side constituting portion and the insertion portion main body to be able to be flexed by an external force.

8. The surgical forceps according to claim 7, wherein the distal-end-side constituting portion is attachable and detachable to and from the insertion portion main body.

9. The surgical forceps according to claim 7, wherein the joint portion can be changed into a state in which a central axis of the distal-end-side constituting portion intersects with a central axis of the insertion portion main body or into a linear state, and can be held in the intersecting state or in the linear state by a holding mechanism.

10. The surgical forceps according to claim 5, wherein the operation rod includes a distal-end-side operation rod having a distal end portion connected to the grasping portion, an operation rod main body having a proximal end portion connected to the first operation portion, and a flexible member having flexibility previously set and connecting the operation rod main body and the distal-end-side operation rod.

11. The surgical forceps according to claim 10, wherein the proximal end portion of the operation rod main body is connected to a movable handle rotatably connected to the first operation portion.

12. The surgical forceps according to claim 11, wherein the first operation portion is provided with a ratchet mechanism for holding a moved position of the movable handle.

13. The surgical forceps according to claim 5, wherein the second operation portion includes a grasping portion opening/closing mechanism configured by the first operation member having one end pivotally supported in a rotatable manner on a proximal end side of the side hole of the opening/closing operation portion main body and the second operation member having one end pivotally supported in a rotatable manner at the other end of the first operation member and having the other end pivotally supported in a rotatable manner at the operation rod.

* * * * *